(12) United States Patent
Jung et al.

(10) Patent No.: US 11,312,691 B2
(45) Date of Patent: Apr. 26, 2022

(54) HETEROCYCLIC COMPOUNDS AND ORGANIC LIGHT EMITTING DEVICE USING THE SAME

(71) Applicant: LG Chem, Ltd., Seoul (KR)

(72) Inventors: Min Woo Jung, Daejeon (KR); Dong Hoon Lee, Daejeon (KR); Seong Mi Cho, Daejeon (KR); Dong Uk Heo, Daejeon (KR); Mi Yeon Han, Daejeon (KR); Jung Ha Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 420 days.

(21) Appl. No.: 16/474,008

(22) PCT Filed: Feb. 21, 2018

(86) PCT No.: PCT/KR2018/002134
§ 371 (c)(1),
(2) Date: Jun. 26, 2019

(87) PCT Pub. No.: WO2018/155904
PCT Pub. Date: Aug. 30, 2018

(65) Prior Publication Data
US 2019/0352270 A1 Nov. 21, 2019

(30) Foreign Application Priority Data

Feb. 21, 2017 (KR) .................. 10-2017-0022903
Feb. 20, 2018 (KR) .................. 10-2018-0020039

(51) Int. Cl.
*C07D 213/24* (2006.01)
*C07D 237/26* (2006.01)
(Continued)

(52) U.S. Cl.
CPC ......... *C07D 251/24* (2013.01); *C07D 213/24* (2013.01); *C07D 239/26* (2013.01);
(Continued)

(58) Field of Classification Search
CPC ... C07D 213/24; C07D 237/26; C07D 251/24
See application file for complete search history.

(56) References Cited

U.S. PATENT DOCUMENTS

2004/0251816 A1 12/2004 Leo et al.
2006/0154105 A1 7/2006 Yamamoto et al.
(Continued)

FOREIGN PATENT DOCUMENTS

CN 101597259 A 12/2009
CN 101875637 A 11/2010
(Continued)

OTHER PUBLICATIONS

Chernyak, et al. (2009).Synthesis of Fluorenes via the Palladium—Catalyzed 5—exo—dig Annulation of o-Alkynylbiaryls. Advanced Synthesis & Catalysis, vol. 351, pp. 1101-1114.
(Continued)

*Primary Examiner* — Vu A Nguyen
(74) *Attorney, Agent, or Firm* — Dentons US LLP

(57) ABSTRACT

The present invention relates to a novel cyclic compound represented by Formula 1, and an organic light emitting device comprising an organic material layer including the novel cyclic compound and having improved efficiency, low driving voltage, and enhanced lifetime characteristic:
(Continued)

[Formula 1]

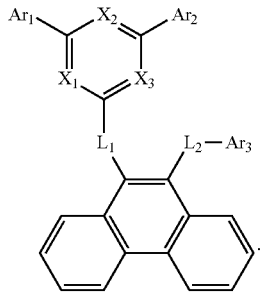

10 Claims, 1 Drawing Sheet

(51) Int. Cl.
| | | |
|---|---|---|
| | *C07D 251/24* | (2006.01) |
| | *H01L 51/00* | (2006.01) |
| | *H01L 51/50* | (2006.01) |
| | *C07D 239/26* | (2006.01) |
| | *C07D 401/10* | (2006.01) |
| | *C07D 401/14* | (2006.01) |
| | *C07D 403/10* | (2006.01) |
| | *C07D 405/10* | (2006.01) |
| | *C07D 409/10* | (2006.01) |

(52) U.S. Cl.
CPC ......... *C07D 401/10* (2013.01); *C07D 401/14* (2013.01); *C07D 403/10* (2013.01); *C07D 405/10* (2013.01); *C07D 409/10* (2013.01); *H01L 51/0054* (2013.01); *H01L 51/0058* (2013.01); *H01L 51/0072* (2013.01); *H01L 51/5072* (2013.01)

(56) References Cited

U.S. PATENT DOCUMENTS

| | | |
|---|---|---|
| 2014/0225072 A1 | 8/2014 | Kim et al. |
| 2014/0299192 A1 | 10/2014 | Lee et al. |
| 2014/0346483 A1 | 11/2014 | Yu et al. |
| 2015/0162543 A1 | 6/2015 | Lee et al. |
| 2016/0141514 A1 | 5/2016 | Lee et al. |
| 2016/0172598 A1 | 6/2016 | Lee et al. |
| 2016/0218298 A1 | 7/2016 | Lee et al. |
| 2017/0018718 A1 | 1/2017 | Jang et al. |
| 2018/0066180 A1 | 3/2018 | Huh et al. |
| 2018/0269402 A1 | 9/2018 | Huh et al. |
| 2018/0315930 A1 | 11/2018 | Han et al. |
| 2019/0055222 A1* | 2/2019 | Han ..................... C07D 251/24 |

FOREIGN PATENT DOCUMENTS

| | | |
|---|---|---|
| CN | 101898996 A | 12/2010 |
| CN | 103531714 A | 1/2014 |
| CN | 103579528 A | 2/2014 |
| JP | 2004002297 A | 1/2004 |
| JP | 2015509954 A | 4/2015 |
| JP | 2016530230 A | 9/2016 |
| KR | 10-2011-0047803 A | 5/2011 |
| KR | 10-2013-073537 A | 7/2013 |
| KR | 10-2015-0024288 A | 3/2015 |
| KR | 10-2015-0027562 A | 3/2015 |
| KR | 1020150115647 A | 10/2015 |
| KR | 10-2010-0050700 A | 5/2016 |
| KR | 10-2016-0050700 A | 5/2016 |
| KR | 10-2016-0060539 A | 5/2016 |
| KR | 10-2016-0111780 A | 9/2016 |
| KR | 10-2016-0126862 A | 11/2016 |
| TW | 201406755 A | 2/2014 |
| WO | 03012890 A2 | 2/2003 |
| WO | 2004063159 A1 | 7/2004 |
| WO | 2012133042 A1 | 10/2012 |
| WO | 2014010823 A | 1/2014 |
| WO | 2015152651 A1 | 10/2015 |
| WO | 2017074053 A1 | 5/2017 |
| WO | WO-2017074053 A1 * | 5/2017 ........... C07D 403/10 |

OTHER PUBLICATIONS

Gong. (2014).Tetraphenylethene-Decorated Carbazoles:Synthesis, Aggregation-Induced Emission, Photo-Oxidation and Electroluminescence, Journal of Materials Chemistry C, vol. 2, pp. 7001-7012.

Iwasaki, et al. (2015). Synthesis of Multisubstituted Triphenylenes and Phenanthrenes by Cascade Reaction of o-Iodobiphenyls or (Z)--Halostyrenes with o-Bromobenzyl Alcohols through Two Sequential C—C Bond Formations Catalyzed by a Palladium Complex. The Journal of Organic Chemistry, xxxx, xxx, xxx-xxx, 17 pages.

He, et al. (2008). Facile Synthesis of 9,10-Diarylphenanthrenes and Poly(9,10-diarylphenanthrene)s, Organic Letters, vol. 10. No. 5. pp. 773-776.

Ma, et al. (2015). Palladium-Catalyzed Annulation of 2,2'-Dibromobiphenyls with Alkynes: Synthesis of Functionalized Phenanthrenes and Dibenzochrysenes, Synlett, vol. 26, pp. 1991-1996.

Lin, et al. (2009). Synthesis of 9,9'-biphenanthryl-10,10'-bis(oxazoline)s and their preliminary evaluations in the Friedel—Crafts alkylations of indoles with nitroalkenes,Tetrahedron, col. 65. pp. 1010-1016.

\* cited by examiner

【FIG. 1】
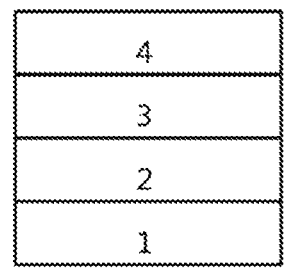
【FIG. 2】
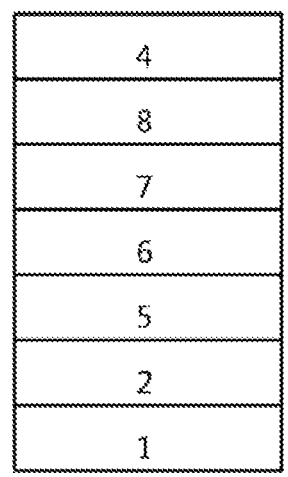

HETEROCYCLIC COMPOUNDS AND ORGANIC LIGHT EMITTING DEVICE USING THE SAME

CROSS-REFERENCE TO RELATED APPLICATION(S)

The present application is a National Phase entry pursuant to 35 U.S.C. § 371 of PCT/KR2018/002134, filed on Feb. 21, 2018, and claims priority to and the benefit of Korean Patent Application No. 10-2017-0022903, filed on Feb. 21, 2017 and Korean Patent Application No. 10-2018-0020039, filed on Feb. 20, 2018 with the Korean Intellectual Property Office, the disclosures of which are incorporated herein by reference in their entirety.

BACKGROUND OF THE INVENTION

Field of the Invention

The present invention relates to a novel heterocyclic compound and an organic light emitting device comprising the same.

Background Art

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently have a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and the electrons meet each other, an exciton is formed, and light is emitted when the exciton falls to a ground state again.

There is a continuing need for the development of new materials for the organic materials used in such organic light emitting devices.

PRIOR ART LITERATURE

Patent Literature (Patent Literature 0001) Korean Patent Laid-open Publication No. 10-2013-073537

DETAILED DESCRIPTION OF THE INVENTION

Technical Problem

It is an object of the present invention to provide a novel heterocyclic compound and an organic light emitting device comprising the same.

Technical Solution

In order to achieve the above object, the present invention provides a compound represented by Formula 1 below:

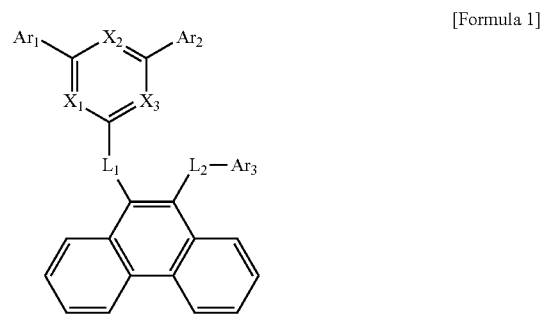

[Formula 1]

in Formula 1 above, $X_1$, $X_2$ and $X_3$ are each independently CH or N, provided that at least one of $X_1$, $X_2$ and $X_3$ is N, $L_1$ is a substituted or unsubstituted $C_{6-60}$ arylene, or a substituted or unsubstituted $C_{5-60}$ heteroarylene containing at least one heteroatom selected from the group consisting of N, O and S, $L_2$ is a single bond, a substituted or unsubstituted $C_{6-60}$ arylene, or a substituted or unsubstituted $C_{5-60}$ heteroarylene containing at least one heteroatom selected from the group consisting of N, O and S, $Ar_1$, $Ar_2$ and $Ar_3$ are each independently a substituted or unsubstituted $C_{6-60}$ aryl, or a substituted or unsubstituted $C_{5-60}$ heteroaryl containing at least one heteroatom selected from the group consisting of N, O and S, wherein said aryl or heteroaryl can be further substituted with a cyano group,

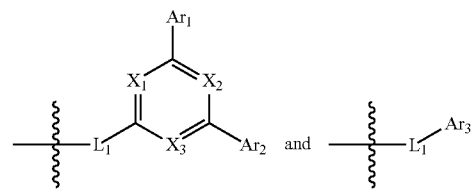

are different from each other.

The present invention also provides an organic light emitting device comprising a first electrode; a second electrode provided at a side opposite to the first electrode; and at least one layer of the organic material layers provided between the first electrode and the second electrode, wherein the at least one layer of the organic material layers includes a compound of the present invention.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8, and a cathode 4.

The compound represented by the Formula 1 can be used as a material of an organic material layer of an organic light emitting device, and can achieve an improvement of the efficiency, a low driving voltage and/or an improvement of the lifetime characteristic when applied to the organic light emitting device. In particular, the compound represented by the Formula 1 can be used as hole injection, hole transport, hole injection and transport, light emission, electron transport, or electron injection materials.

DETAILED DESCRIPTION OF THE EMBODIMENTS

The present invention provides a compound represented by Formula 1 below:

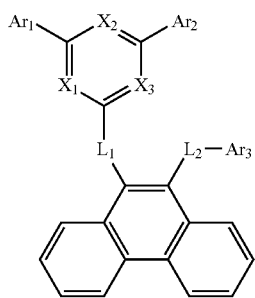

[Formula 1]

in Formula 1 above, $X_1$, $X_2$ and $X_3$ are each independently CH or N, provided that at least one of $X_1$, $X_2$ and $X_3$ is N, $L_1$ is a substituted or unsubstituted $C_{6-60}$ arylene, or a substituted or unsubstituted $C_{5-60}$ heteroarylene containing at least one heteroatom selected from the group consisting of N, O and S, $L_2$ is a single bond, a substituted or unsubstituted $C_{6-60}$ arylene, or a substituted or unsubstituted $C_{5-60}$ heteroarylene containing at least one heteroatom selected from the group consisting of N, O and S, $Ar_1$, $Ar_2$ and $Ar_3$ are each independently a substituted or unsubstituted $C_{6-60}$ aryl, or a substituted or unsubstituted $C_{5-60}$ heteroaryl containing at least one heteroatom selected from the group consisting of N, O and S, wherein said aryl or heteroaryl can be further substituted with a cyano group, provided that the two substituents,

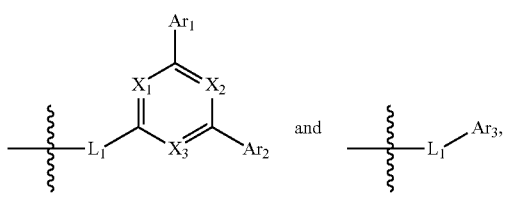

of the phenanthrylene are different from each other.

In the present specification,

means a bond connected to another substituent group.

As used herein, the term "substituted or unsubstituted" means that substitution is performed by one or more substituent groups selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a heterocyclic group containing at least one of N, O, and S atoms, or there is no substituent group, or substitution is performed by a substituent group where two or more substituent groups of the exemplified substituent groups are linked or there is no substituent group. For example, the term "substituent group where two or more substituent groups are linked" may be a biphenyl group. That is, the biphenyl group may be an aryl group, or may be interpreted as a substituent group where two phenyl groups are connected.

In the present specification, the number of carbon atoms in a carbonyl group is not particularly limited, but is preferably 1 to 40 carbon atoms. Specifically, the carbonyl group may be compounds having the following structures, but is not limited thereto.

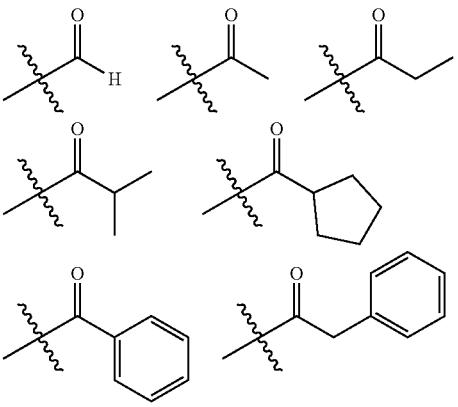

In the present specification, the ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be compounds having the following structures, but is not limited thereto.

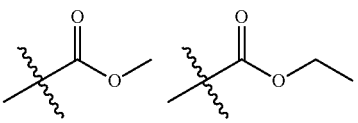

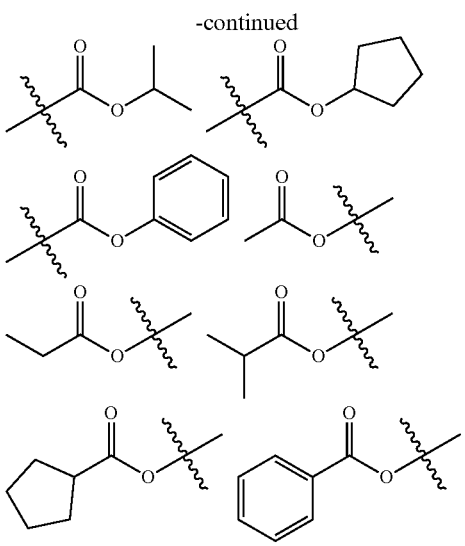

In the present specification, the number of carbon atoms in an imide group is not particularly limited, but is preferably 1 to 25. Specifically, the imide group may be compounds having the following structures, but is not limited thereto.

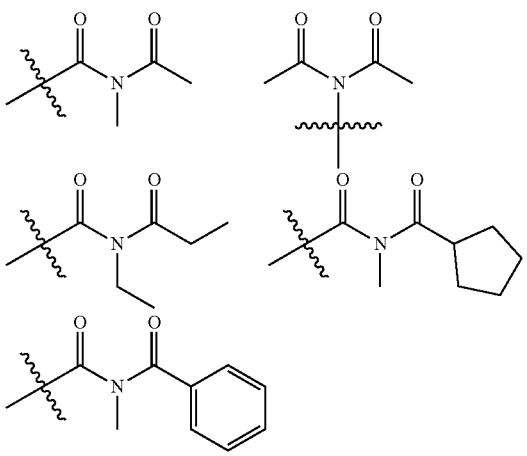

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes a trimethylboron group, a triethylboron group, a t-butyldimethylboron group, a triphenylboron group, a phenylboron group, and the like, but is not limited thereto.

In the present specification, examples of a halogen group include fluorine, chlorine, bromine, or iodine.

In the present specification, the alkyl group may be a straight chain or a branched chain, and the number of carbon atoms thereof is not particularly limited, but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl, and the like, but are not limited thereto.

In the present specification, the alkenyl group may be a straight chain or a branched chain, and the number of carbon atoms thereof is not particularly limited, but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, the cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and may be a monocyclic aryl group or a polycyclic aryl group. According to one embodiment, the aryl group has 6 to 30 carbon atoms. According to one embodiment, the aryl group has 6 to 20 carbon atoms. The aryl group may be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrycenyl group, a fluorenyl group or the like, but is not limited thereto.

In the present specification, a fluorenyl group may be substituted, and two substituent groups may be linked with each other to form a spiro structure. In the case where the fluorenyl group is substituted,

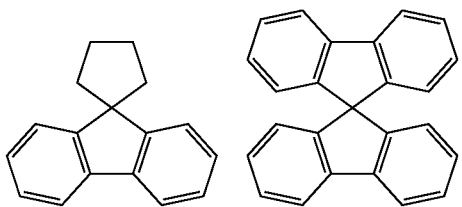

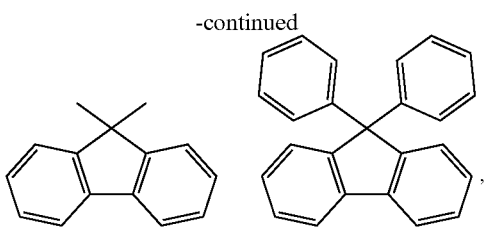

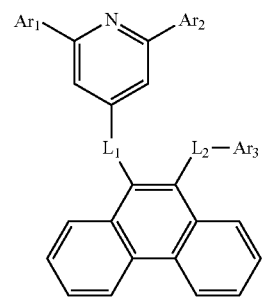
[Formula 1-1]

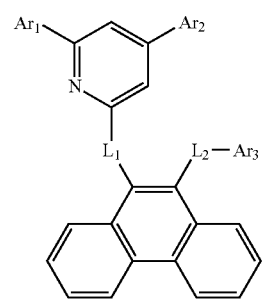
[Formula 1-2]

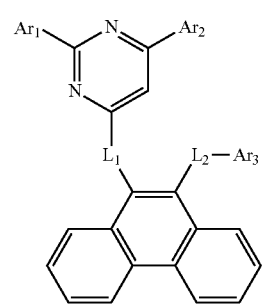
[Formula 1-3]

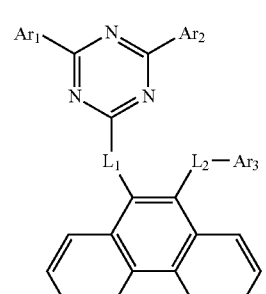
[Formula 1-4]

and the like can be formed. However, the structure is not limited thereto.

In the present specification, the heterocyclic group is a heterocyclic group containing at least one of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamines can be applied to the aforementioned description of the heterocyclic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocycle is not a monovalent group but formed by combining two substituent groups.

Preferably, the compound represented by the Formula 1 may be a compound represented by any one of Formulas 1-1 to 1-4 below.

in Formulas 1-1 to 1-4,
$L_1$, $L_2$, $Ar_1$, $Ar_2$ and $Ar_3$ are as defined above.
Preferably, $L_1$ may be any one selected from the group consisting of the following:

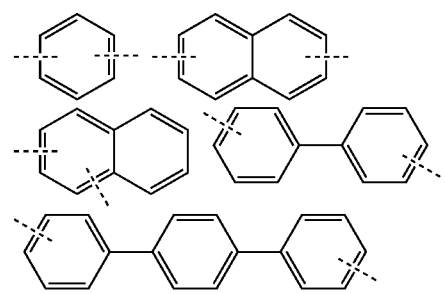

-continued

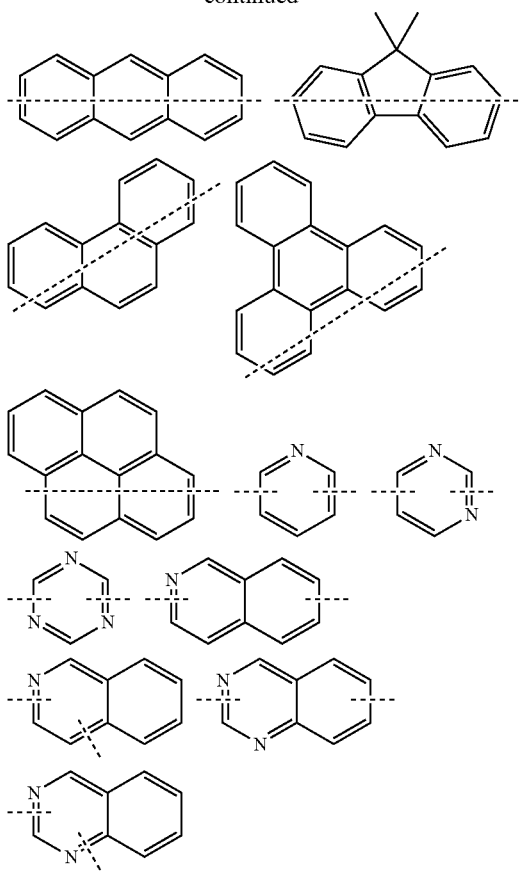

More preferably, L₁ may be any one selected from the group consisting of

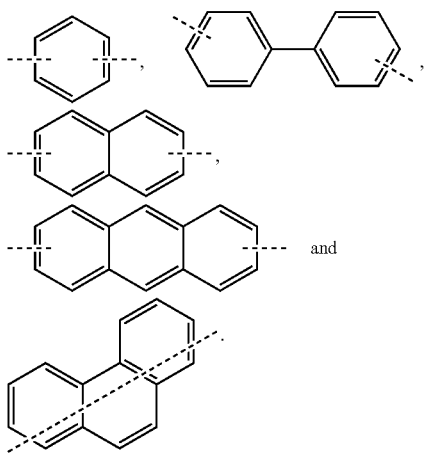

Preferably, L₂ may be a single bond or any one selected from the group consisting of the following:

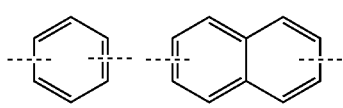

-continued

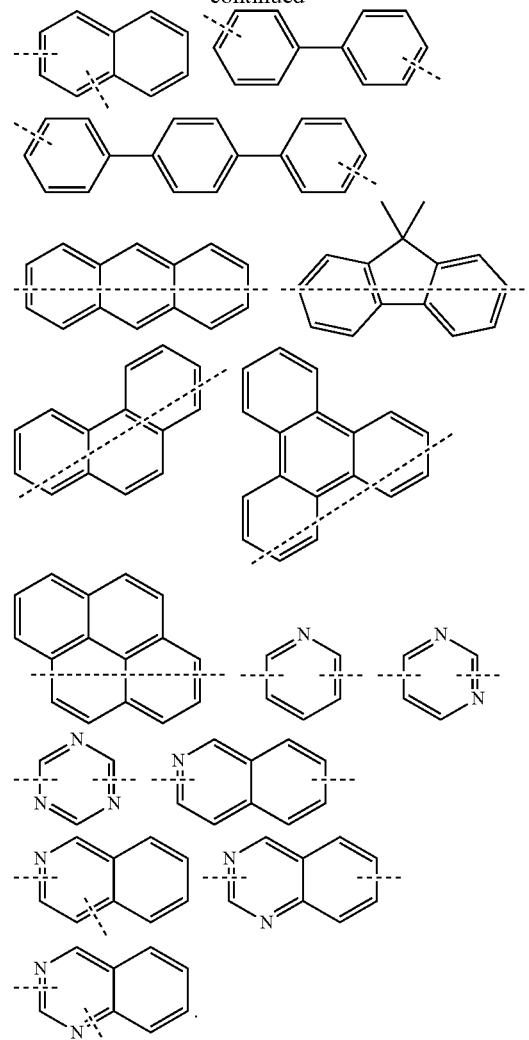

More preferably, L₂ may be any one selected from the group consisting of a single bond,

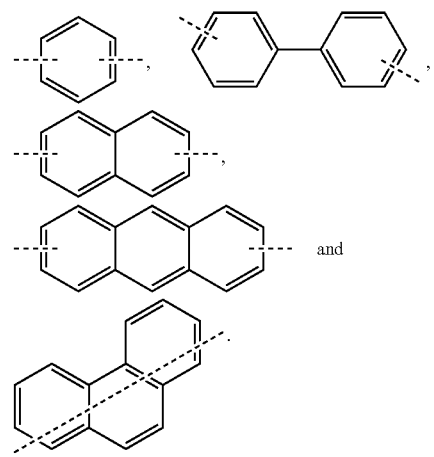

Preferably, Ar₁, Ar₂ and Ar₃ may be each independently any one selected from the group consisting of the following:

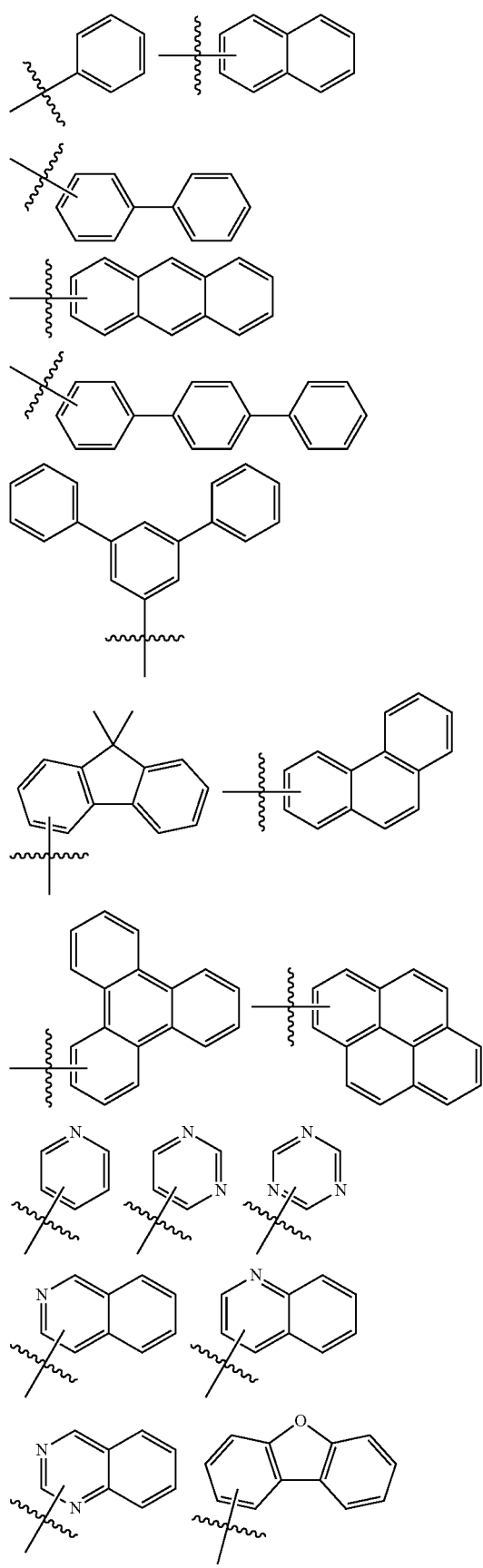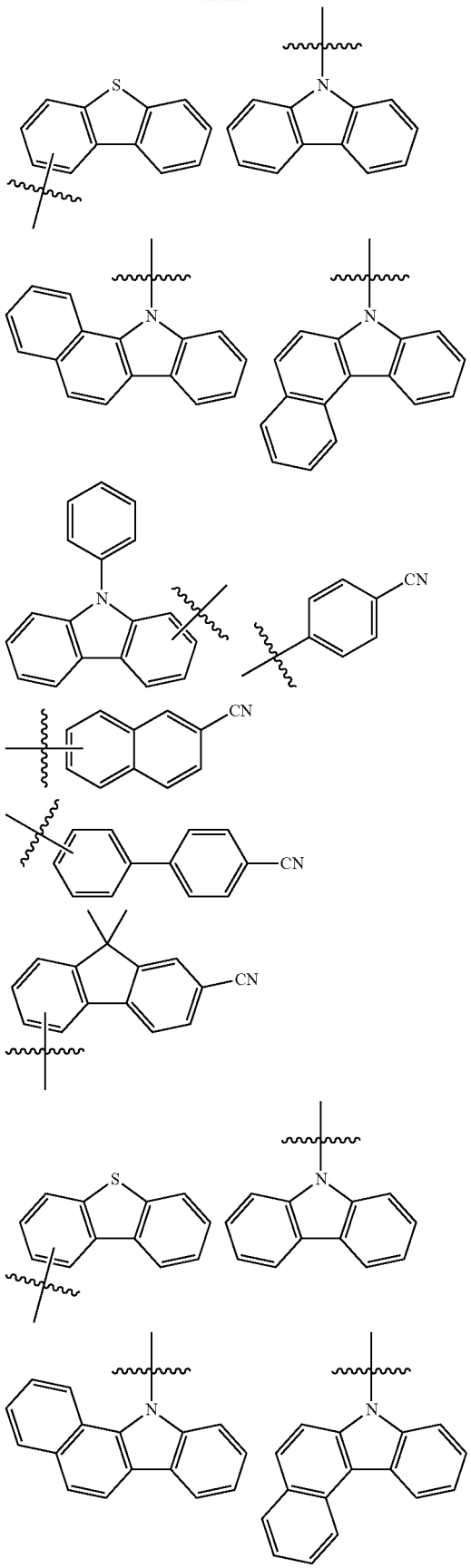

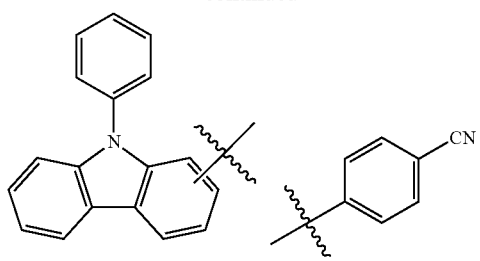
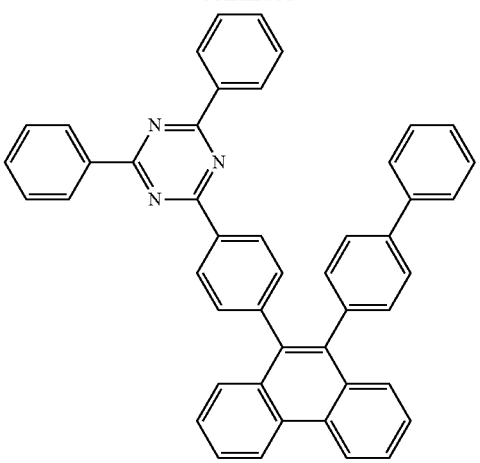
Preferably, the compound represented by the Formula 1 may be any one selected from the group consisting of the following:
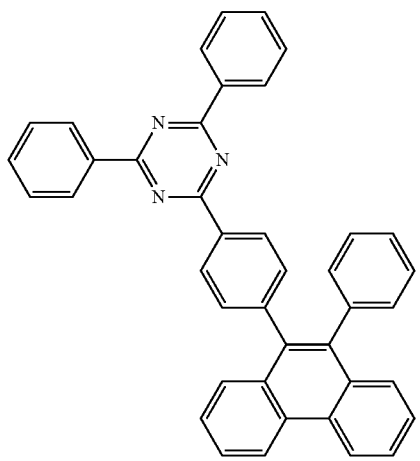

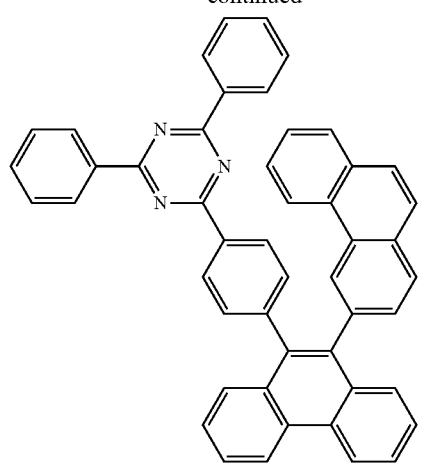
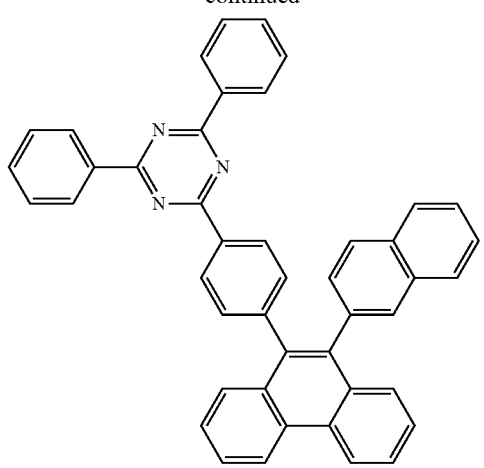
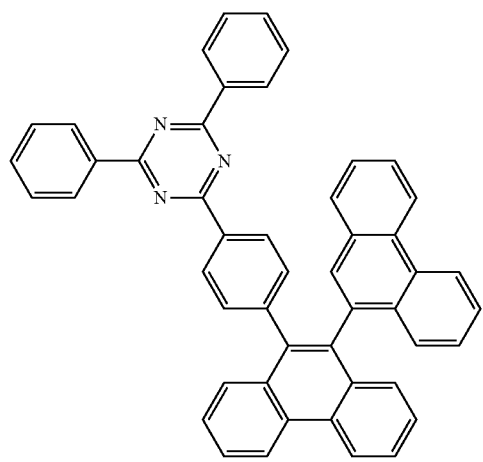
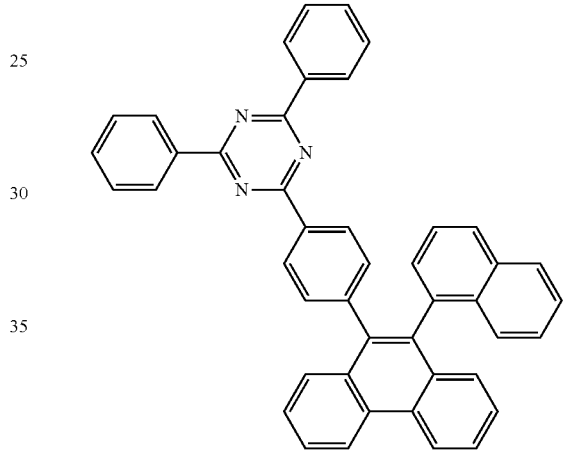
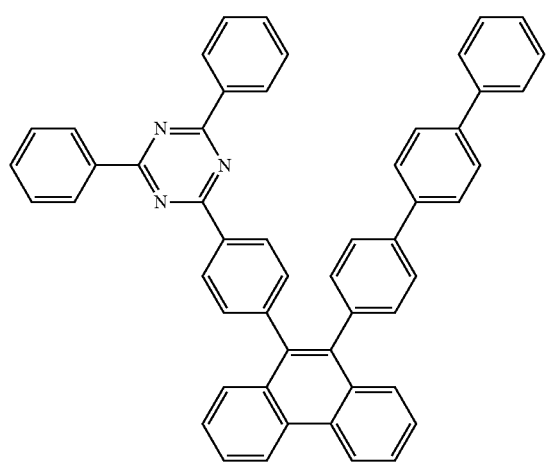
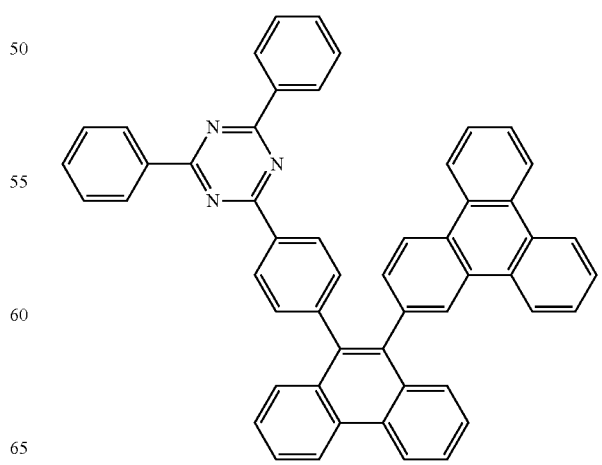

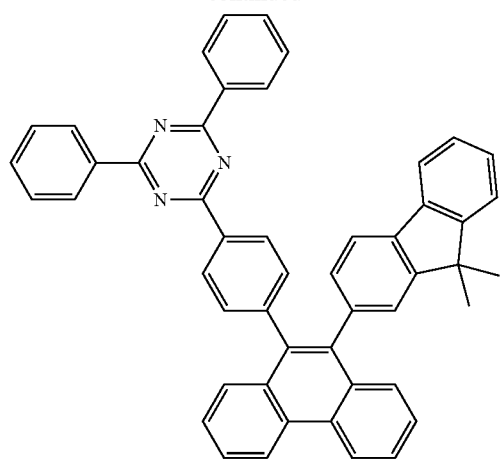
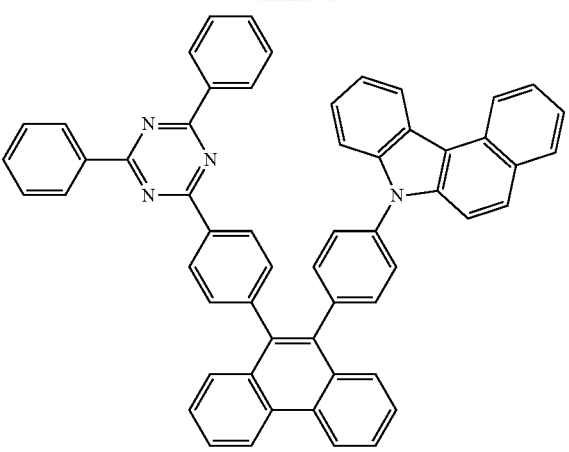
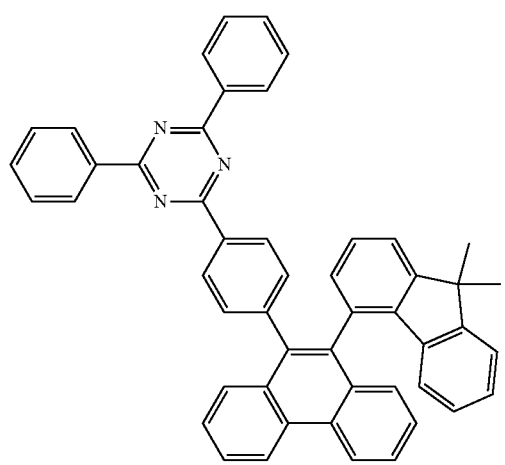
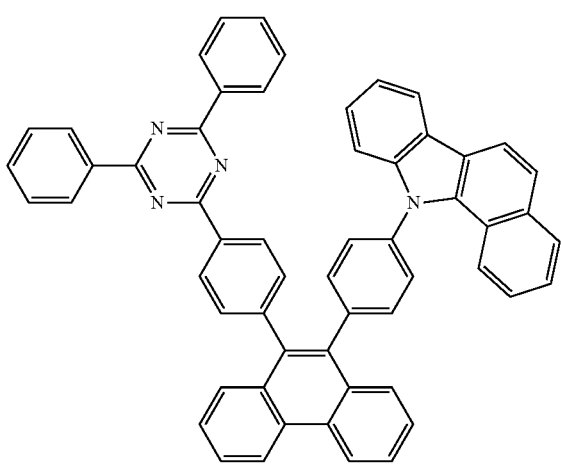
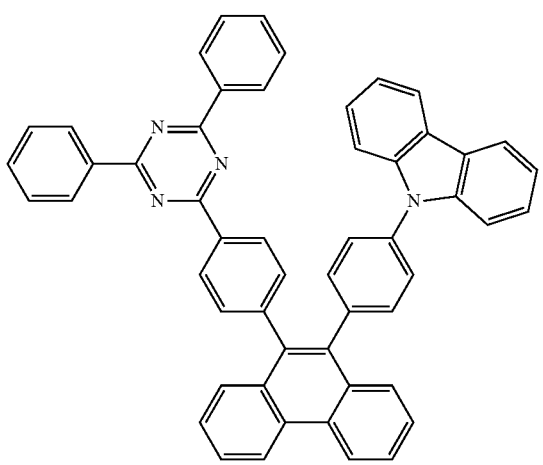
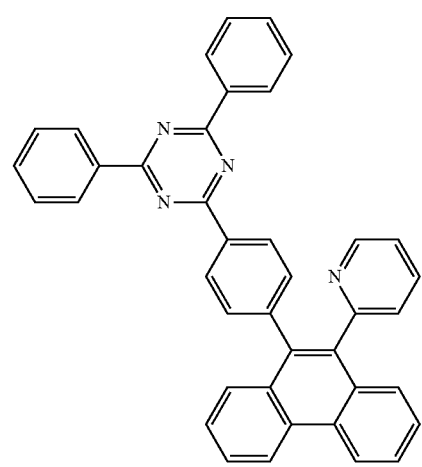

-continued
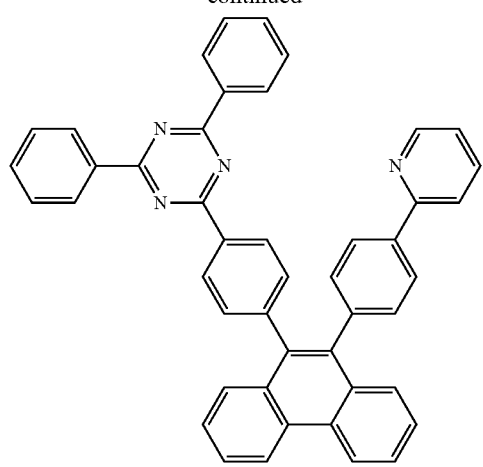
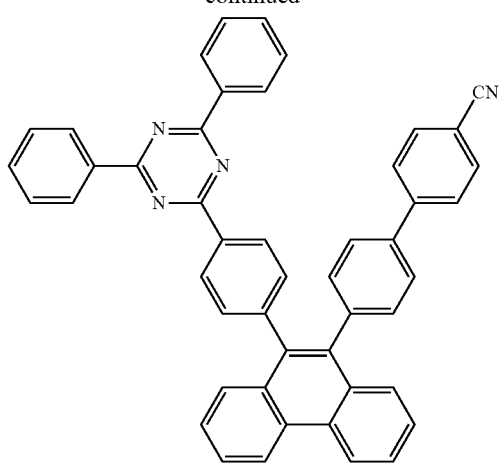
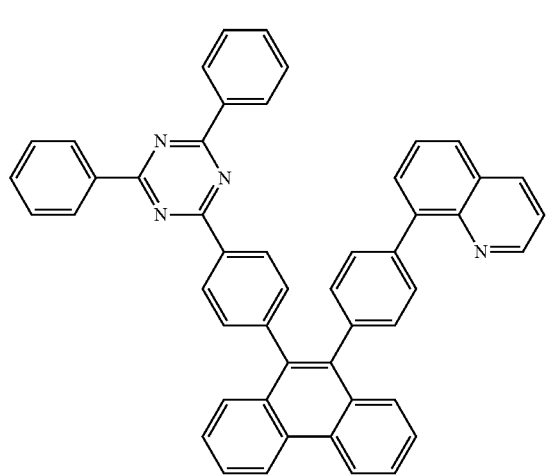
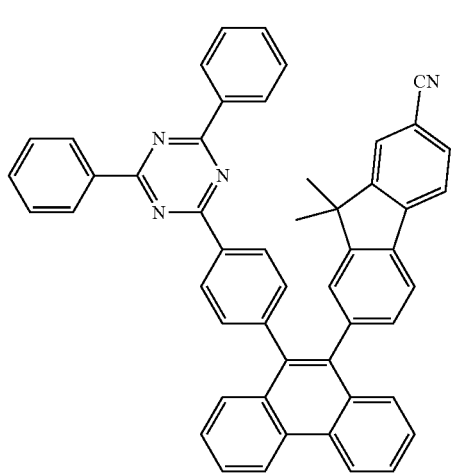
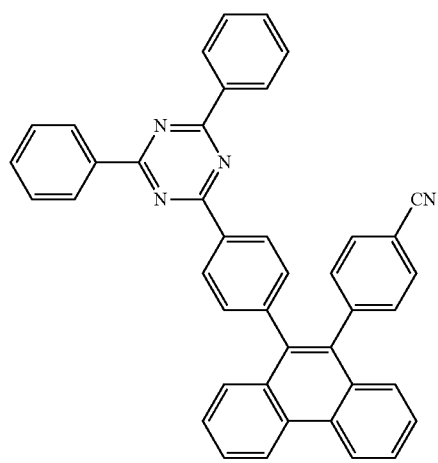
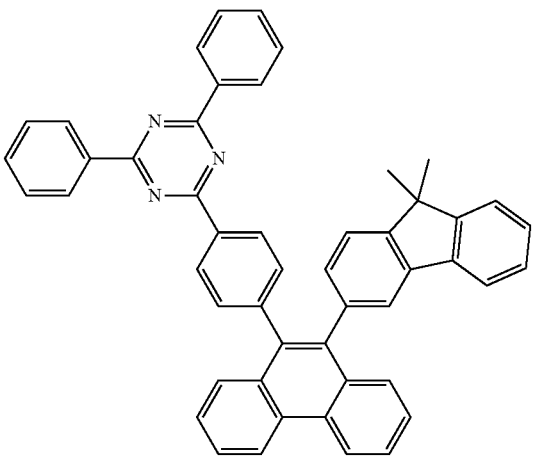

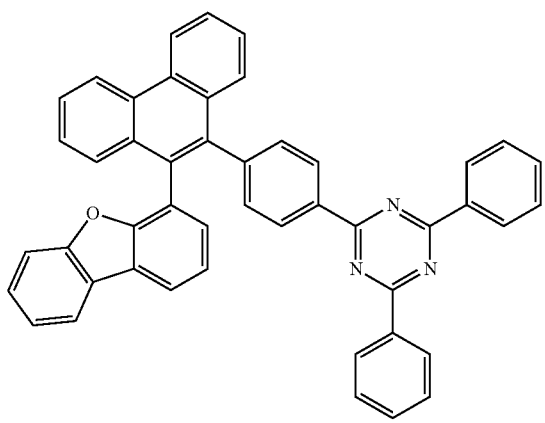
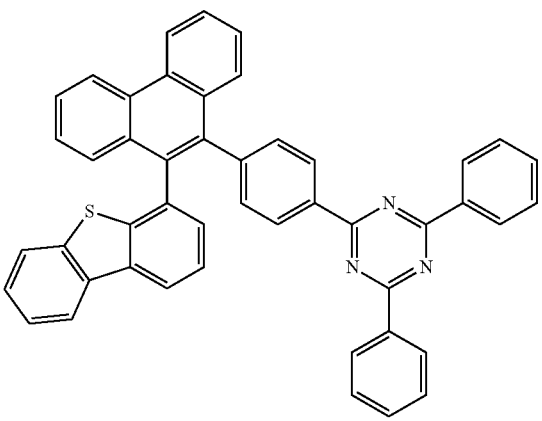
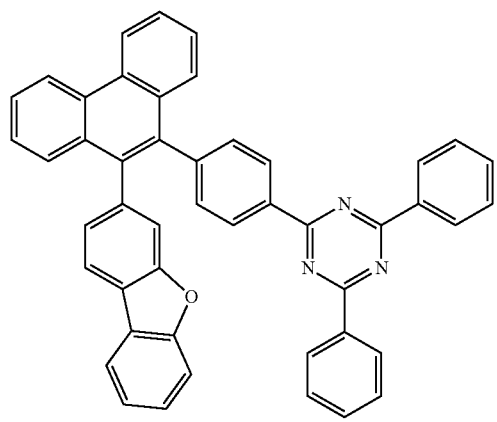
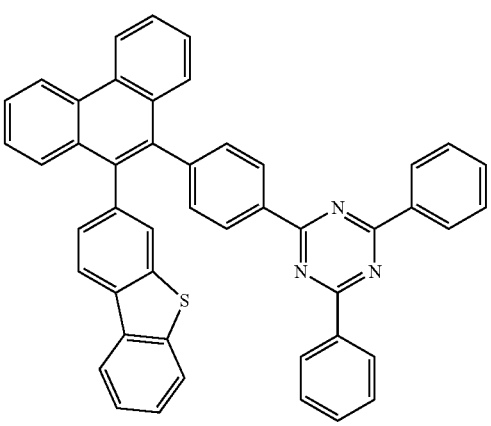
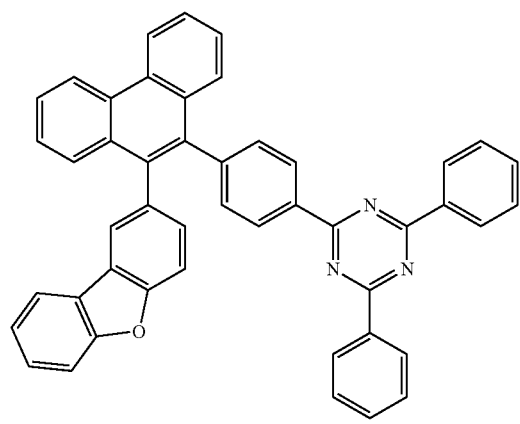
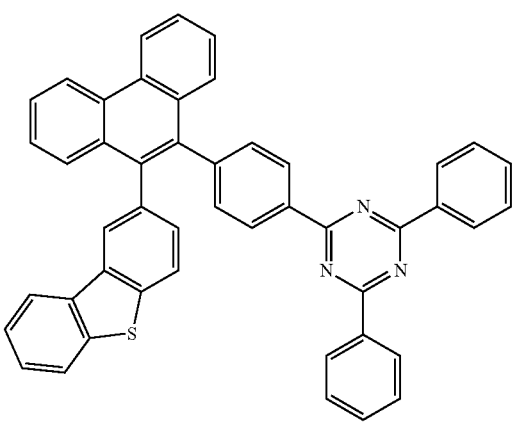
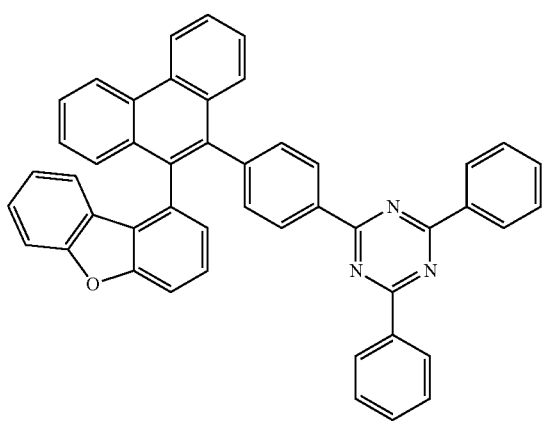
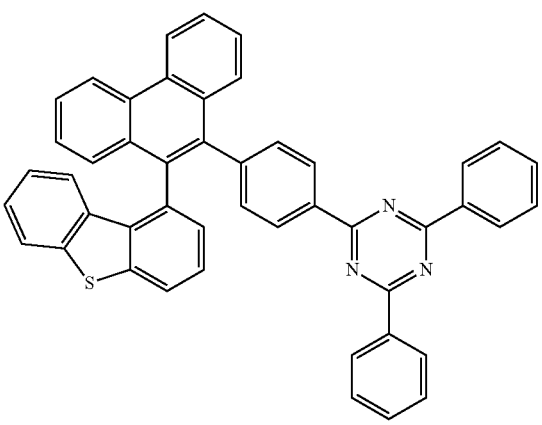

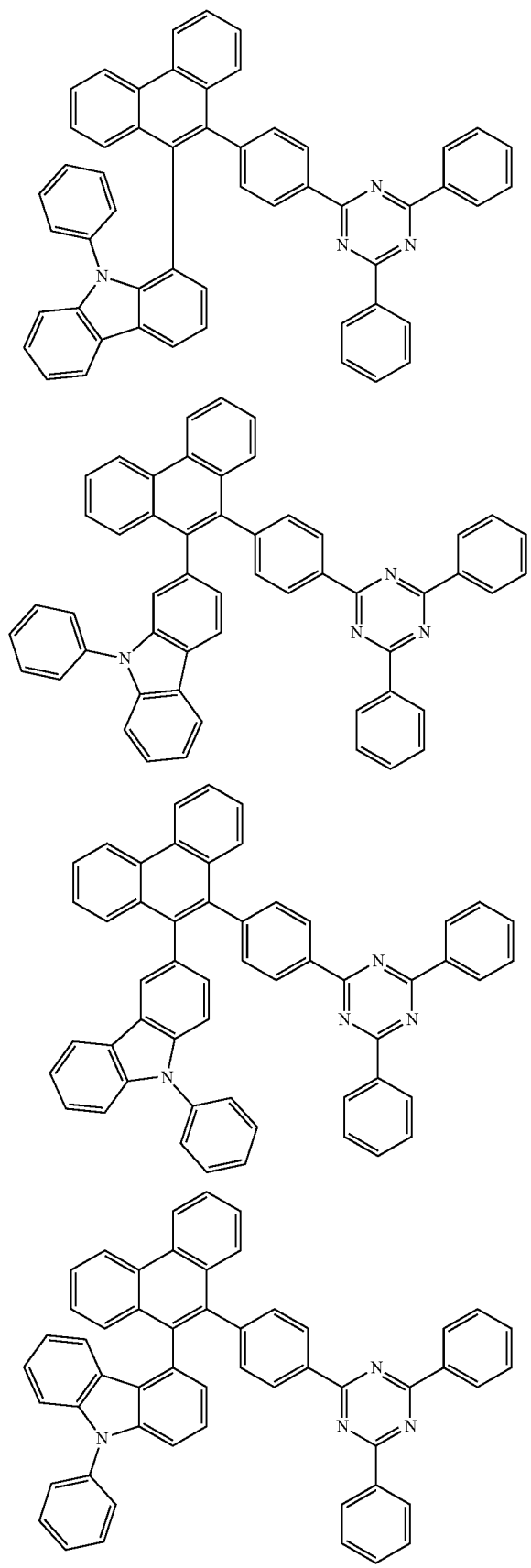
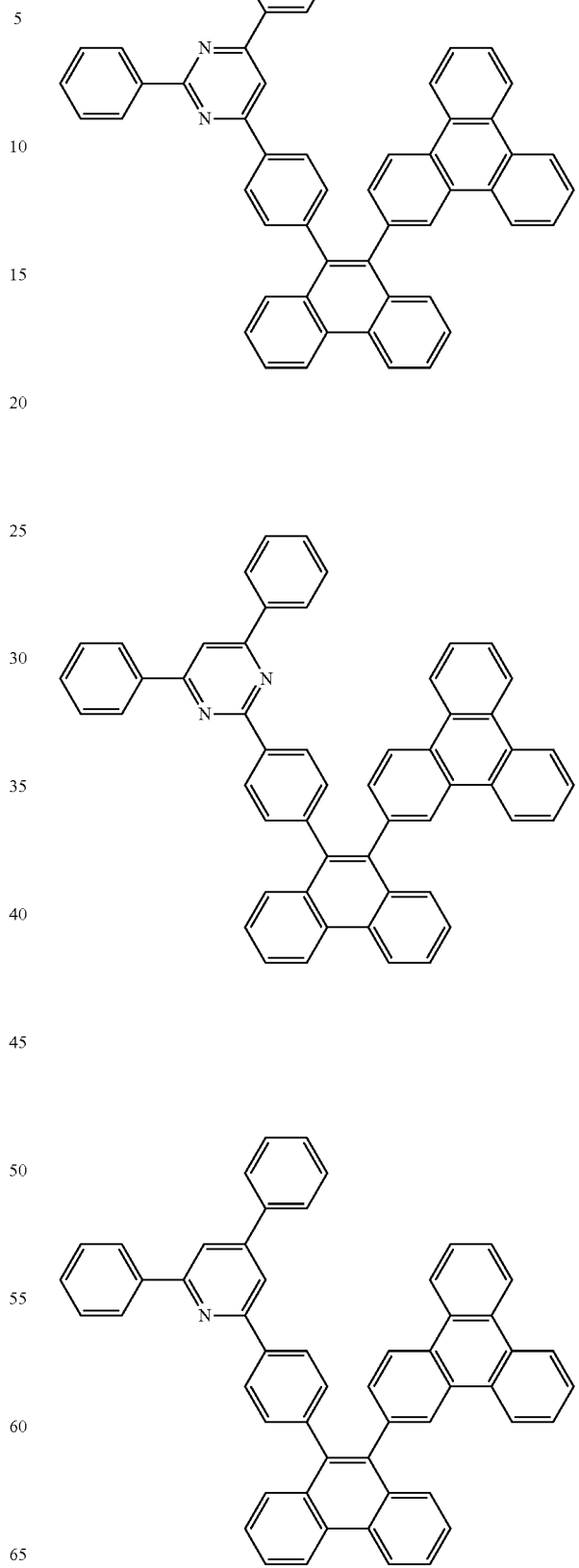

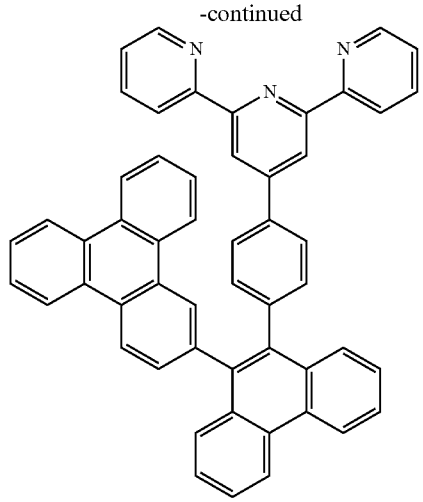

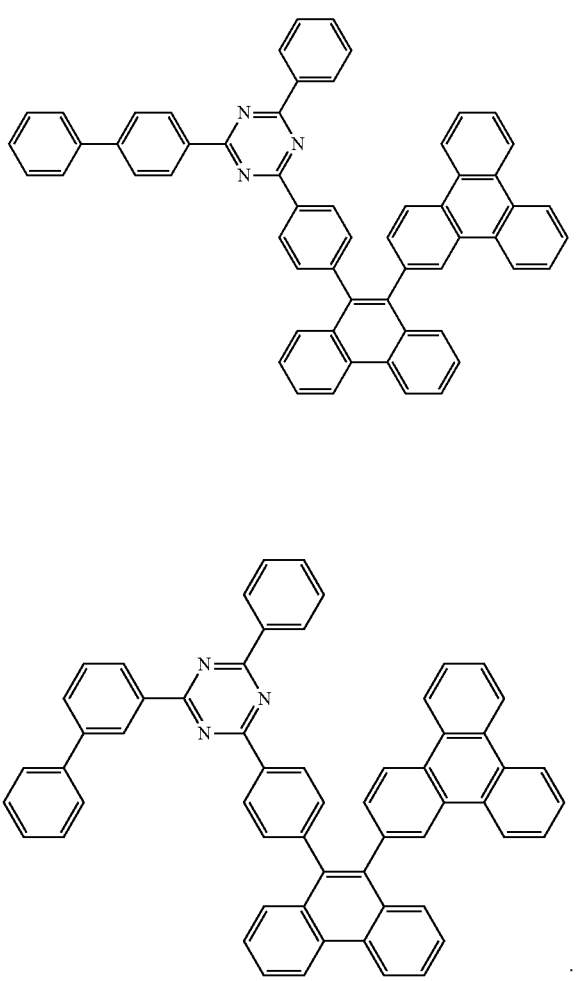

exhibiting excellent heat resistance in driving devices and also suppressing crystallization. Therefore, the organic light emitting device using the same can have a high efficiency, a low driving voltage, a high luminance and a long lifetime.

Further, the compound represented by Formula 1 may be prepared according to the preparation method as shown in the following Reaction Schemes 1A to 1C. The above preparation method can be further specified in the preparation examples to be described later.

[Reaction Scheme 1A]

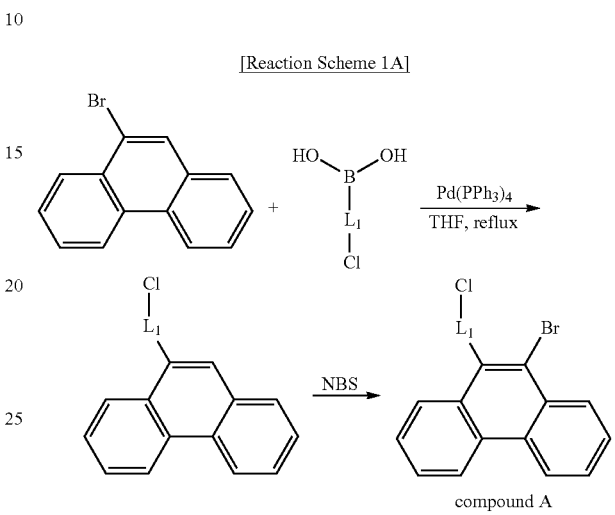

[Reaction Scheme 1B]

The compound represented by the Formula 1 has a phenanthrylene basic structure containing a triazine (pyridine, pyrimidine) substituent, and both substituents of the phenanthrylene have an asymmetric structure, thereby

[Reaction Scheme 1C]

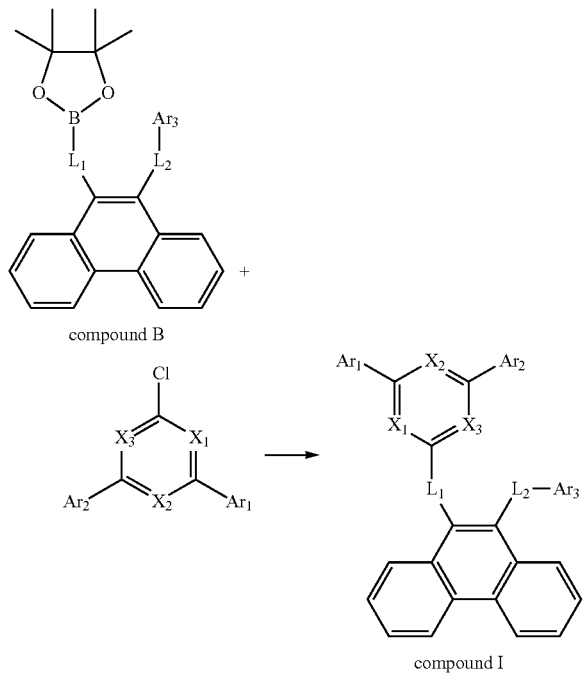

compound I in Reaction Schemes 1A to 1C, $X_1$, $X_2$, $X_3$, $L_1$, $L_2$, $Ar_1$ and $Ar_2$ are defined above.

The compound represented by Formula 1 can be prepared by appropriately substituting the starting material, the type of the reactor, and the type of the catalyst depending on the structure of the compounds to be prepared with reference to the Reaction Schemes 1A to 1C.

In addition, the present invention provides an organic light emitting device comprising the compound represented by Formula 1. In one example, the present invention provides an organic light emitting device comprising a first electrode; a second electrode provided at a side opposite to the first electrode; and at least one layer of organic material layers provided between the first electrode and the second electrode, wherein the at least one layer of the organic material layers includes a compound represented by Formula 1.

The organic material layer of the organic light emitting device of the present invention may have a single layer structure, but it may have a multilayered structure in which two or more organic material layers are stacked. For example, the organic light emitting device of the present invention may have a structure comprising a hole injection layer, a hole transport layer, a light emitting layer, an electron transport layer, an electron injection layer and the like as the organic material layer. However, the structure of the organic light emitting device is not limited thereto, and it may include a smaller number of organic layers.

Further, the organic material layer may include a hole injection layer, a hole transport layer, or a layer simultaneously performing hole injection and transport, wherein the hole injection layer, the hole transport layer, and the layer simultaneously performing hole injection and transport include a compound represented by Formula 1.

Further, the organic material layer may include a light emitting layer, wherein the light emitting layer includes a compound represented by Formula 1.

Further, the organic material layer may include an electron transport layer or an electron injection layer, wherein the electron transport layer or the electron injection layer includes a compound represented by Formula 1.

Further, the electron transport layer, the electron injection layer and the layer simultaneously performing an electron injection and an electron transport include a compound represented by Formula 1. In particular, the compound represented by Formula I according to the present invention has excellent thermal stability and has a deep HOMO level of 6.0 eV or more, high triplet energy (ET), and hole stability. Further, when the compound represented by Formula 1 is used for an organic material layer capable of performing electron injection and electron transport at the same time, an n-type dopant used in the art can be mixed and used.

Further, the organic material layer may include a light emitting layer or an electron transport layer, wherein the electron transport layer may include a compound represented by Formula 1.

Further, the organic light emitting device according to the present invention may be a normal type organic light emitting device in which an anode, at least one organic material layer, and a cathode are sequentially stacked on a substrate. Further, the organic light emitting device according to the present invention may be an inverted type organic light emitting device in which a cathode, at least one organic material layer and an anode are sequentially stacked on a substrate. For example, the structure of an organic light emitting device according to an embodiment of the present invention is illustrated in FIGS. 1 and 2.

FIG. 1 shows an example of an organic light emitting device comprising a substrate 1, an anode 2, a light emitting layer 3, and a cathode 4. In such a structure, the compound represented by Formula 1 may be included in the light emitting layer.

FIG. 2 shows an example of an organic light emitting device comprising a substrate 1, an anode 2, a hole injection layer 5, a hole transport layer 6, a light emitting layer 7, an electron transport layer 8, and a cathode 4. In such a structure, the compound represented by Formula 1 may be included in at least one layer of the hole injection layer, the hole transport layer, the light emitting layer and the electron transport layer.

The organic light emitting device according to the present invention may be manufactured by materials and methods known in the art, except that at least one layer of the organic material layers includes the compound represented by Formula 1. In addition, when the organic light emitting device includes a plurality of organic material layers, the organic material layers may be formed of the same material or different materials.

For example, the organic light emitting device according to the present invention can be manufactured by sequentially stacking a first electrode, an organic material layer and a second electrode on a substrate. In this case, the organic light emitting device may be manufactured by depositing a metal, metal oxides having conductivity, or an alloy thereof on the substrate by using a PVD (physical vapor deposition) method such as a sputtering method or an e-beam evaporation method to form the anode, forming an organic material layer including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, an organic material layer and an anode material on a substrate.

In addition, the compound represented by Formula 1 may be formed into an organic layer by a solution coating method as well as a vacuum deposition method at the time of manufacturing an organic light emitting element. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

For example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SNO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has an ability of transporting the holes, a hole injecting effect in the anode and an excellent hole injecting effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is a material capable of emitting light in the visible light region by combining holes and electrons respectively transported from the hole transport layer and the electron transport layer, and having good quantum efficiency for fluorescence or phosphorescence. Specific examples include 8-hydroxy-quinoline aluminum complex ($Alq_3$); carbazole-based compounds; dimerized styryl compounds; BAlq; 10-hydroxybenzoquinoline-metal compounds; benzoxazole, benzothiazole and benzimidazole-based compounds; poly(p-phenylenevinylene) (PPV)-based polymers; spiro compounds; polyfluorene, rubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, and fluoranthene compounds. Examples of heterocyclic compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specific examples of the aromatic amine derivatives include substituted or unsubstituted fused aromatic ring derivatives having an arylamino group, examples thereof include pyrene, anthracene, chrysene, and periflanthene having the arylamino group, and the like, the styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer receiving the electrons from the electron injection layer and transporting the electrons to the light emitting layer, the electron transport material is a material that can receive the electrons well from the cathode and transport the electrons to the light emitting layer, and a material having large mobility to the electrons is suitable. Specific examples thereof include an 8-hydroxyquinoline Al complex; a complex including $Alq_3$; an organic radical compound; a hydroxyflavone-metal complex, and the like, but are not limited thereto. The electron transport layer may be used together with a predetermined desired cathode material as used according to the prior art. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer injecting the electrons from the electrode, and a compound which has an ability of transporting the electrons, an electron injecting effect from the cathode, and an excellent electron injecting effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and its derivative, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris (2-methyl-8-hydroxyquinolinato)aluminum, tris(8-hydroxyquinolinato)gallium, bis(10-hydroxybenzo[h]quinolinato) beryllium, bis(10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium, and the like, but are not limited thereto.

The organic light emitting device according to the present invention may be a front side emission type, a back side emission type, or a double side emission type according to the used material.

In addition, the compound represented by Formula 1 may be included in an organic solar cell or an organic transistor in addition to an organic light emitting device.

The preparation of the compound represented by Formula 1 and the organic light emitting device comprising the same will be described in detail in the following examples. However, these examples are presented for illustrative purposes only, and the scope of the present invention is not limited thereto.

PREPARATION EXAMPLE

Preparation Example 1: Preparation of Compound 1

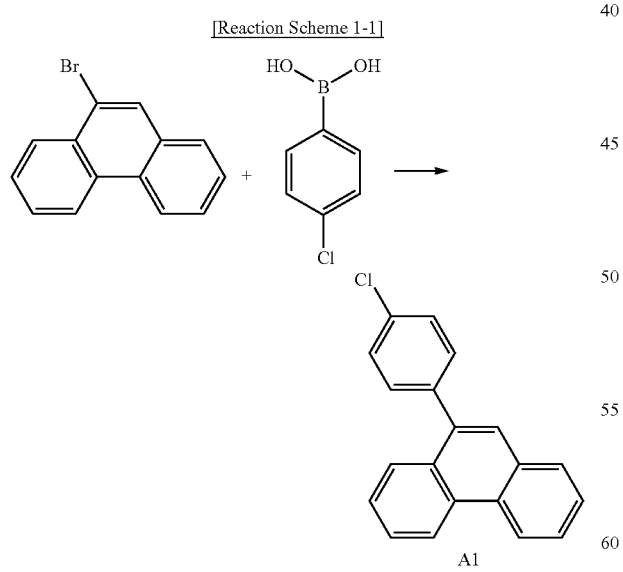

9-Bromophenanthrene (50 g, 195 mmol) and (4-chlorophenyl)boronic acid (33.5 g, 215 mmol) were dissolved in tetrahydrofuran (500 mL). 2 M solution of sodium carbonate (162 mL) and tetrakis(triphenylphosphine)palladium (0) [Pd(PPh$_3$)$_4$](6.8 g, 5.9 mmol) were added thereto and refluxed for 12 hours. After completion of the reaction, the mixture was cooled to room temperature, and the obtained mixture was extracted three times with water and toluene. The toluene layer was separated, dried over magnesium sulfate and filtered. The filtrate was distilled under reduced pressure, and the resulting mixture was recrystallized three times using chloroform and ethanol to obtain Compound A1 (28.1 g, yield 50%; MS: [M+H]$^+$=289).

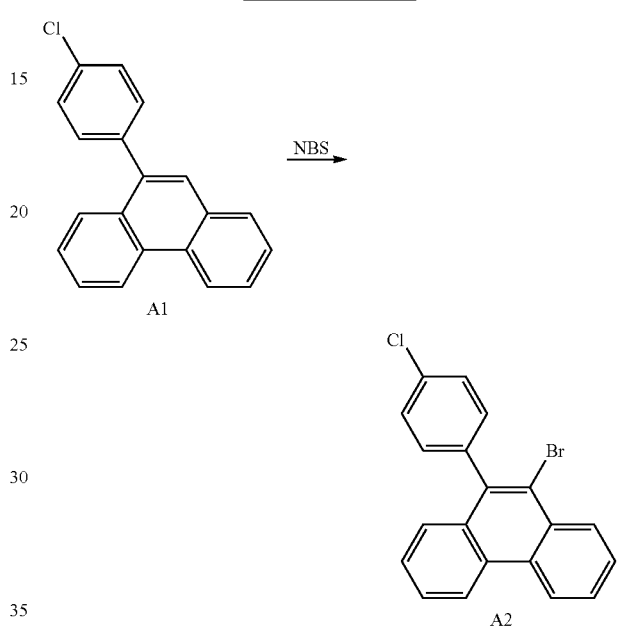

Compound A1 (28.1 g, 98 mmol) was dissolved in dimethylformamide (140 mL) and then cooled to 0° C. After that, N-bromosuccinamide (17.4 g, 98 mmol) was dissolved in 34 ml of DMF and then slowly added dropwise. Subsequently, the temperature was gradually raised, and then the mixture was stirred at room temperature for 1 hour. After completion of the reaction, the reaction mixture was washed once with sodium thiosulfate solution and once with water, dried over magnesium sulfate, and filtered. The filtrate was distilled under reduced pressure and purified by column chromatography to obtain Compound A2 (25 g, yield 70%; MS: [M+H]$^+$=367).

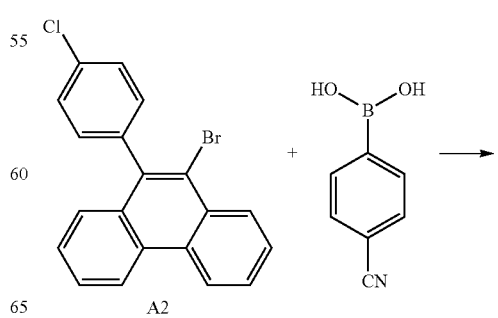

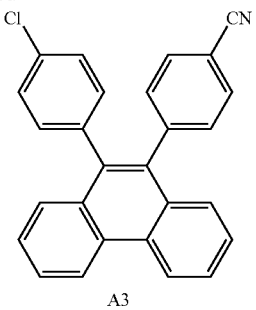

After Compound A2 (20.0 g, 55 mmol) and (4-cyanophenyl)boronic acid (8.8 g, 60 mmol) were dispersed in tetrahydrofuran (200 mL), 2 M solution of potassium carbonate (82 mL, 164 mL) was added and tetrakistriphenylphosphinepalladium [Pd(PPh$_3$)$_4$] (1.9 g, 3 mol %) was added thereto, and then stirred and refluxed for 4 hours. The temperature was lowered to room temperature and the resulting solid was filtered. The filtered solid was recrystallized from tetrahydrofuran and ethyl acetate, filtered and then dried to produce Compound A3 (16.4 g, yield 77%; MS: [M+H]$^+$=390).

[Reaction Scheme 1-4]

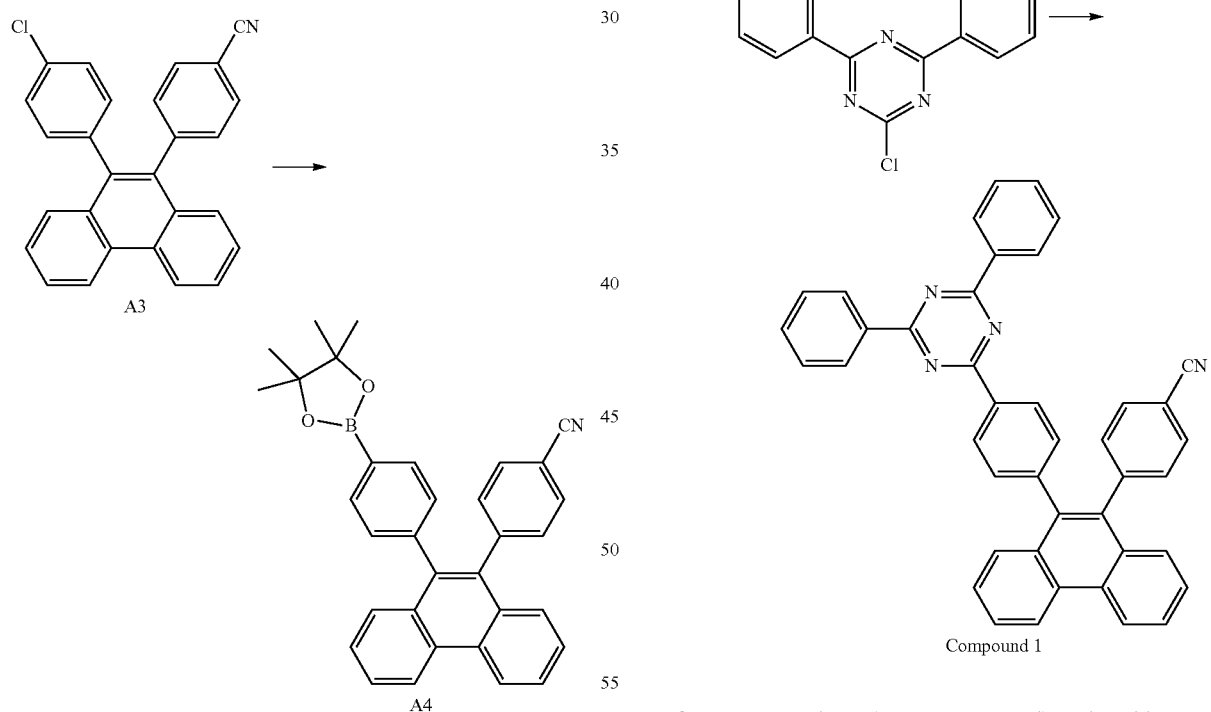

Compound A3 (15 g, 39 mmol), bis(pinacolato)dibron (10.8 g, 42 mmol), potassium acetate (11.4 g, 115 mmol), and bis(tricyclohexylphosphine)palladium diacetate(0) [Pd(OAc)2(PCy3)2] (0.9 g, 3 mol %) was added to dioxane (200 mL) and refluxed for 12 hours. After completion of the reaction, the reaction mixture was cooled to room temperature and distilled under reduced pressure to remove the solvent. This was dissolved in chloroform and washed three times with water, then the organic layer was separated and dried with magnesium sulfate. This was distilled under reduced pressure to produce compound A4 (16.3 g, yield 88%; MS: [M+H]$^+$=482).

[Reaction Scheme 1-5]

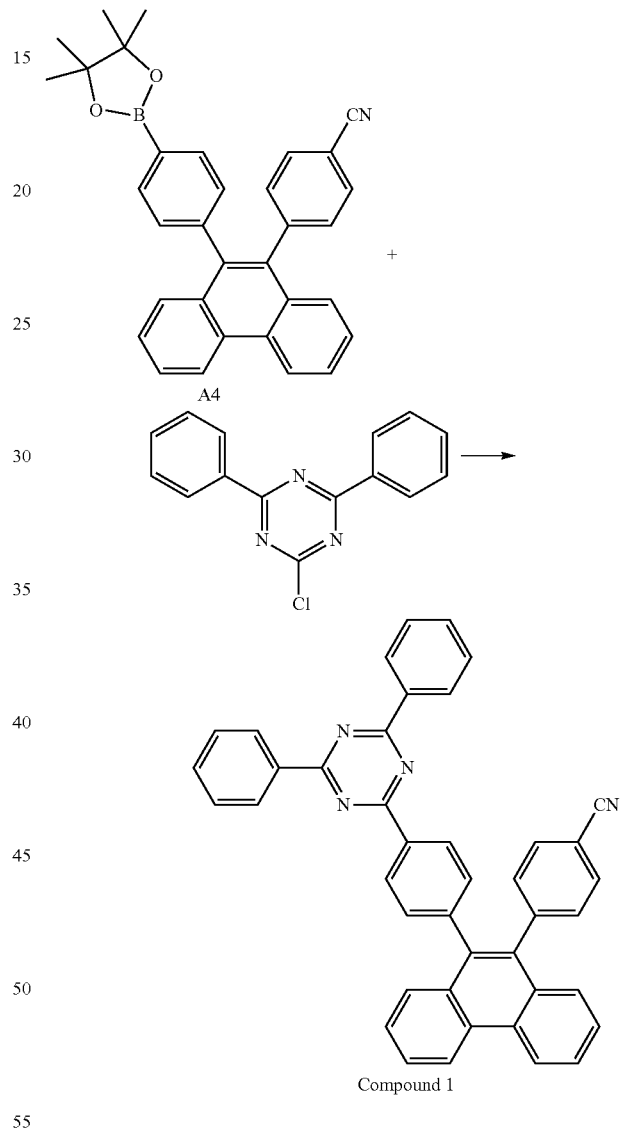

Compound 1

After Compound A4 (16.2 g, 34 mmol) and 2-chloro-4,6-diphenyl-1,3,5-triazine (9 g, 34 mmol) were dispersed in tetrahydrofuran (200 mL), 2M potassium carbonate aqueous solution (aq. K$_2$CO$_3$) (50 mL, 101 mmol) was added and tetrakistriphenylphosphinepalladium [Pd(PPh$_3$)$_4$] (1.2 g, 3 mol %) were added thereto, and then stirred and refluxed for 5 hours. The temperature was lowered to room temperature and the solid formed was filtered. The filtered solid was recrystallized from chloroform and ethyl acetate, filtered, and then dried to produce Compound 1 (9.5 g, yield 48%; MS: [M+H]$^+$=587).

Preparation Example 2: Preparation of Compound 2

[Reaction Scheme 2-1]

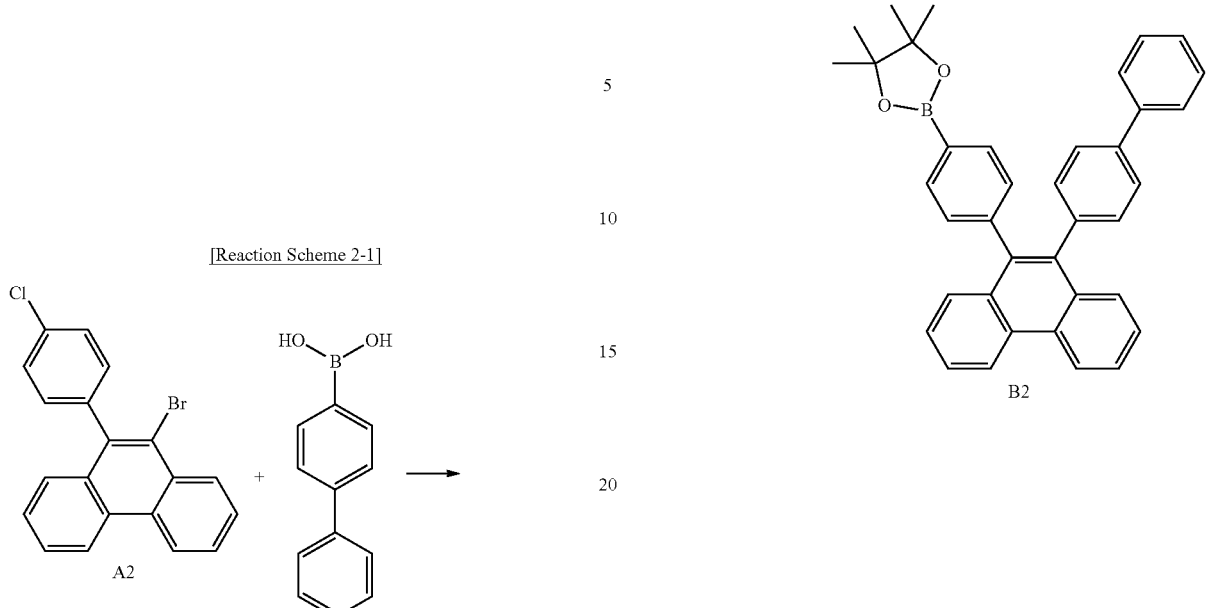

Compound B1 (19.0 g, yield 79%; MS: [M+H]$^+$=441) was prepared in the same manner as in the preparation of Compound A3, except that [1,1'-biphenyl]-4-boronic acid (11.9 g, 60 mmol) was used instead of (4-cyanophenyl) boronic acid.

[Reaction Scheme 2-2]

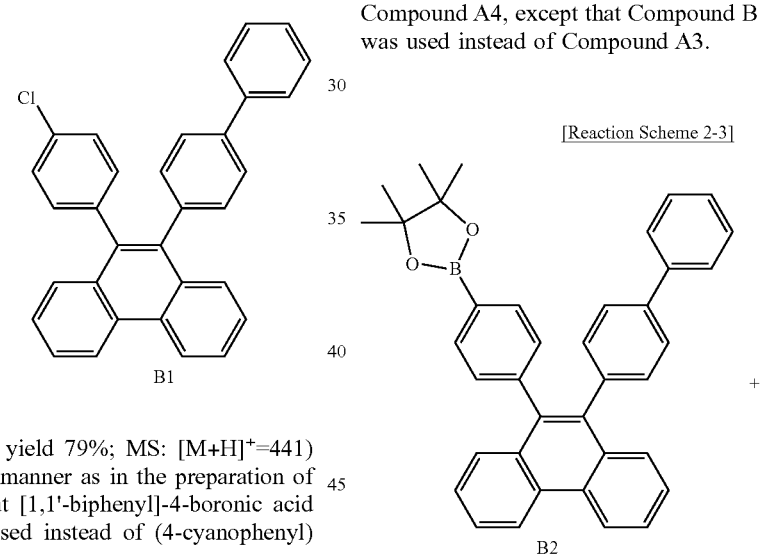

Compound B2 (19.0 g, yield 91%; MS: [M+H]$^+$=532) was prepared in the same manner as in the preparation of Compound A4, except that Compound B1 (15 g, 34 mmol) was used instead of Compound A3.

[Reaction Scheme 2-3]

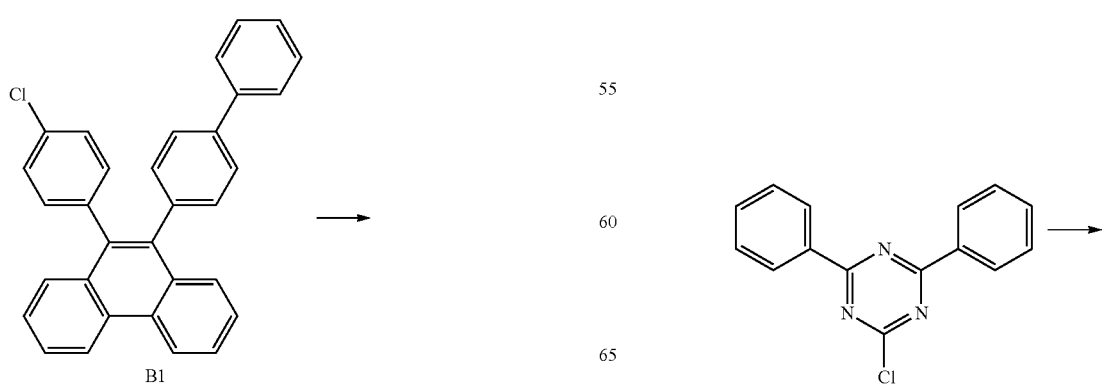

-continued

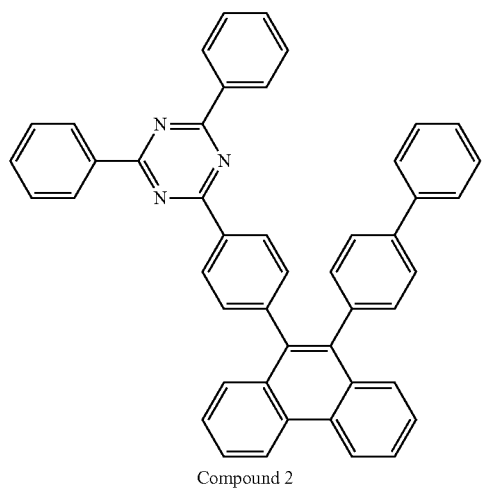
Compound 2

Compound 2 (12.9 g, yield 60%; MS: [M+H]$^+$=638) was prepared in the same manner as in the preparation of Compound 1, except that Compound B2 (17.9 g, 34 mmol) was used instead of Compound A4.

Preparation Example 3: Preparation of Compound 3

[Reaction Scheme 3-1]

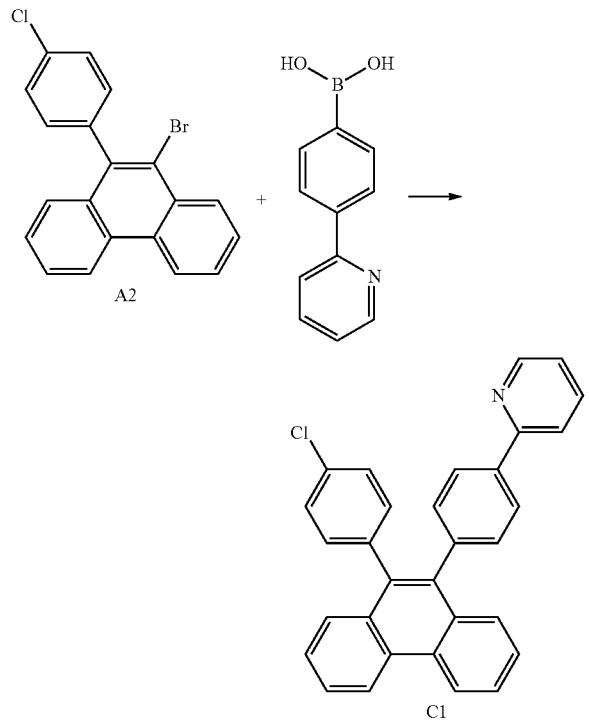

Compound C1 (19.0 g, yield 81%; MS: [M+H]$^+$=442) was prepared in the same manner as in the preparation of Compound A3, except that (4-(pyridin-2-yl)phenyl)boronic acid (11.9 g, 60 mmol) was used instead of (4-cyanophenyl)boronic acid.

[Reaction Scheme 3-2]

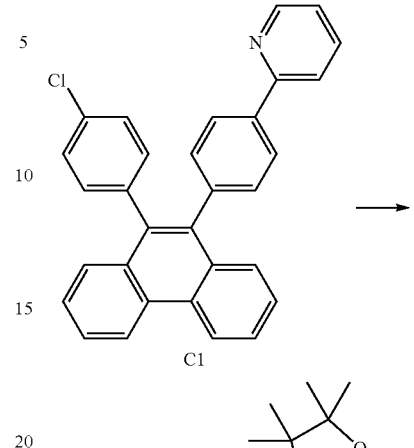
C1

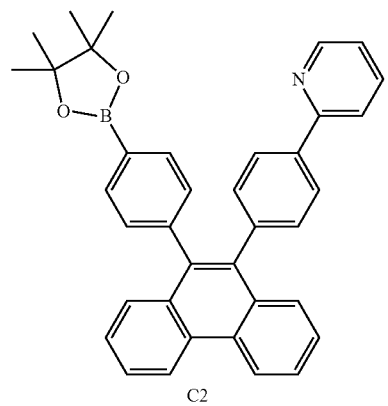
C2

Compound C2 (18.1 g, yield 88%; MS: [M+H]$^+$=533) was prepared in the same manner as in the preparation of Compound A4, except that Compound C1 (15 g, 34 mmol) was used instead of Compound A3.

[Reaction Scheme 3-3]

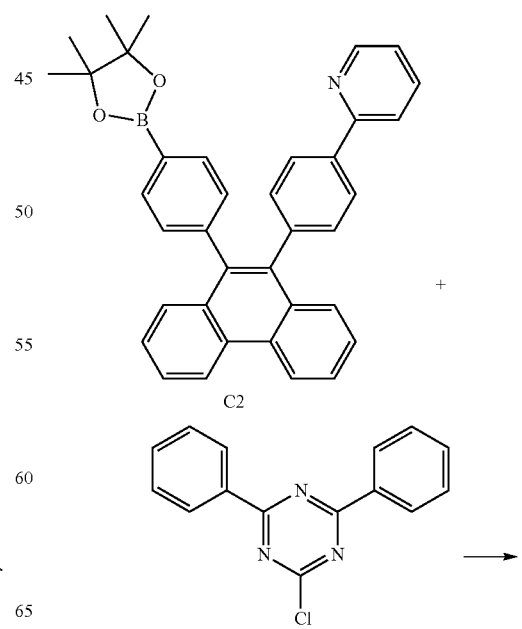

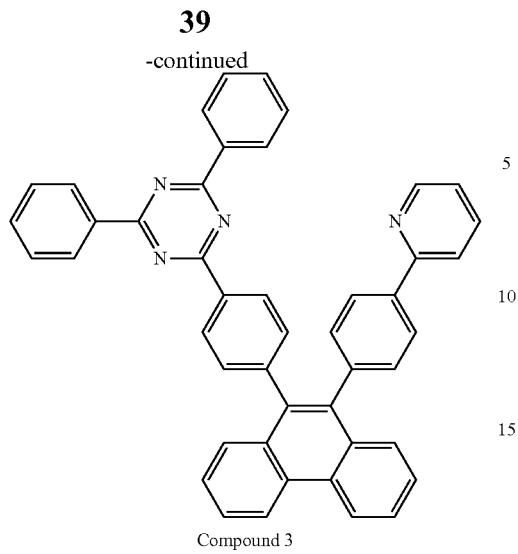

Compound 3

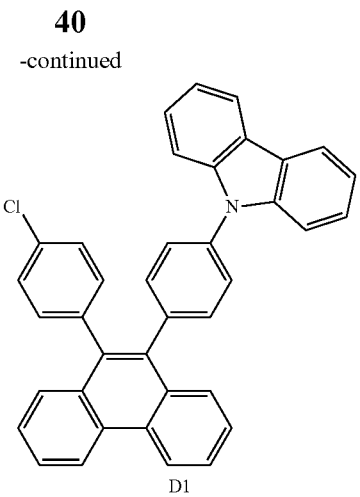

D1

Compound D1 (22.0 g, yield 76%; MS: [M+H]$^+$=530) was prepared in the same manner as in the preparation of Compound A3, except that (4-(9H-carbazol-9-yl)phenyl boronic acid (17.3 g, 60 mmol) was used instead of (4-cyanophenyl)boronic acid.

Compound 3 (9.7 g, yield 45%; MS: [M+H]$^+$=639) was prepared in the same manner as in the preparation of Compound 1, except that Compound C2 (17.9 g, 34 mmol) was used instead of Compound A4.

Preparation Example 4: Preparation of Compound 4

[Reaction Scheme 4-1]

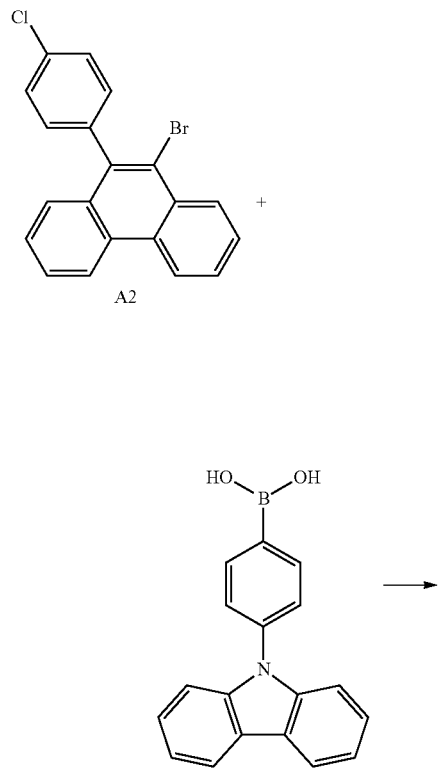

[Reaction Scheme 4-2]

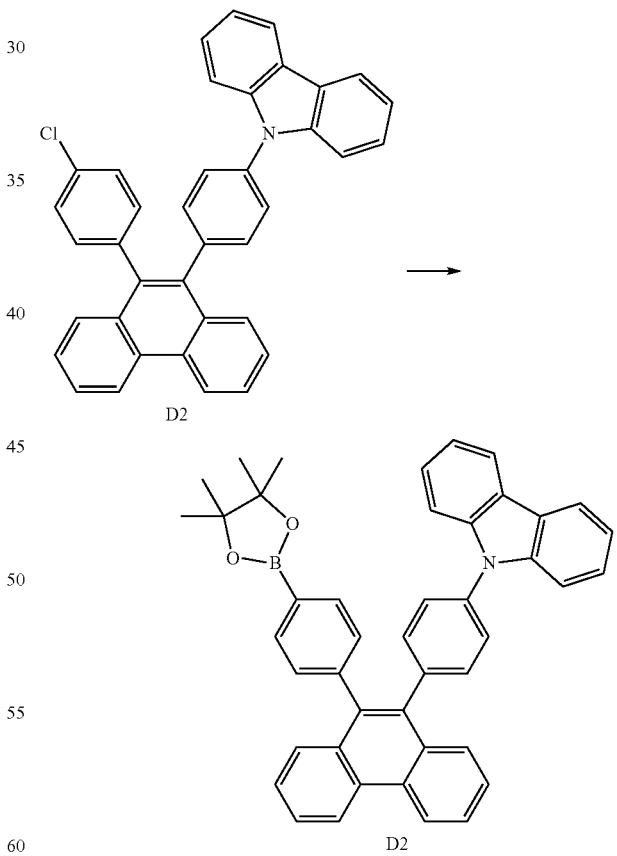

Compound D2 (21.3 g, yield 89%; MS: [M+H]$^+$=622) was prepared in the same manner as in the preparation of Compound A4, except that Compound D1 (15 g, 34 mmol) was used instead of Compound A3.

[Reaction Scheme 4-3]

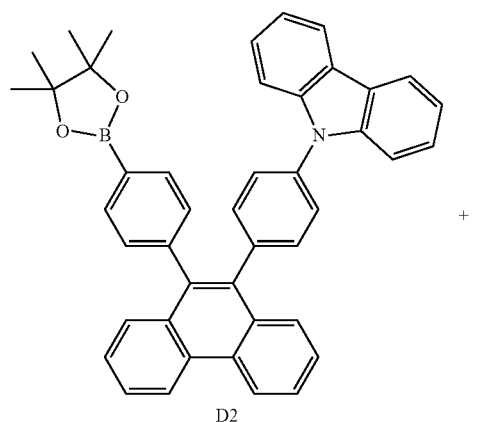

+

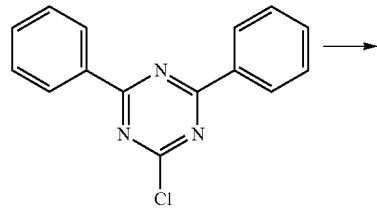

→

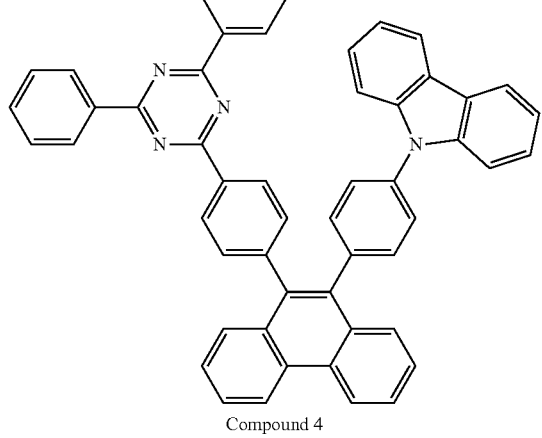

Compound 4

Compound 4 (15.4 g, yield 63%; MS: [M+H]$^+$=727) was prepared in the same manner as in the preparation of Compound 1, except that Compound D2 (20.9 g, 34 mmol) was used instead of Compound A4.

Preparation Example 5: Preparation of Compound 5

[Reaction Scheme 5-1]

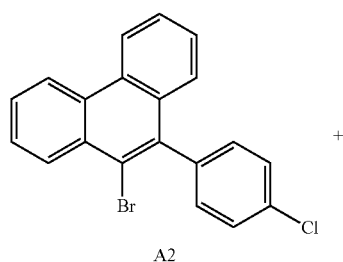

A2

+

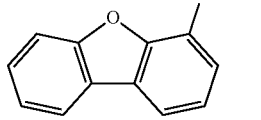

E1

Compound E1 (21.3 g, yield 89%; MS: [M+H]$^+$=455) was prepared in the same manner as in the preparation of Compound A3, except that dibenzo[b,d]furan-4-yl bronic acid (12.7 g, 60 mmol) was used instead of (4-cyanophenyl) boronic acid.

[Reaction Scheme 5-2]

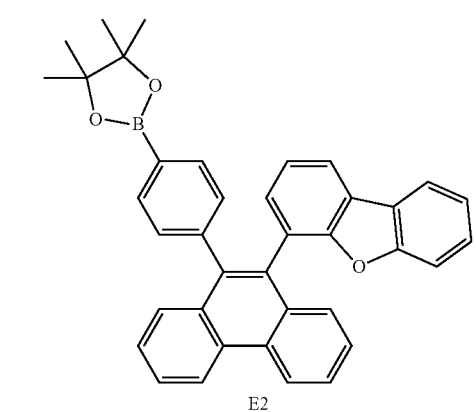

Compound E2 (21.1 g, yield 93%; MS: [M+H]$^+$=547) was prepared in the same manner as in the preparation of Compound A4, except that Compound E1 (15 g, 33 mmol) was used instead of Compound A3.

[Reaction Scheme 5-3]

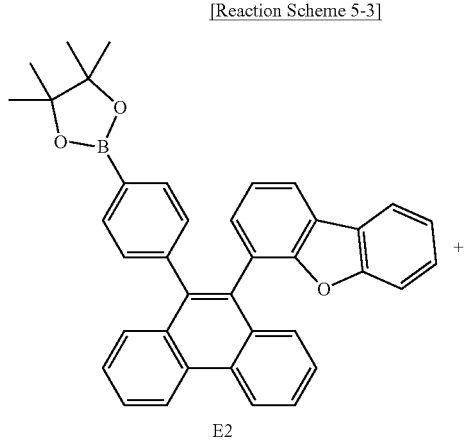

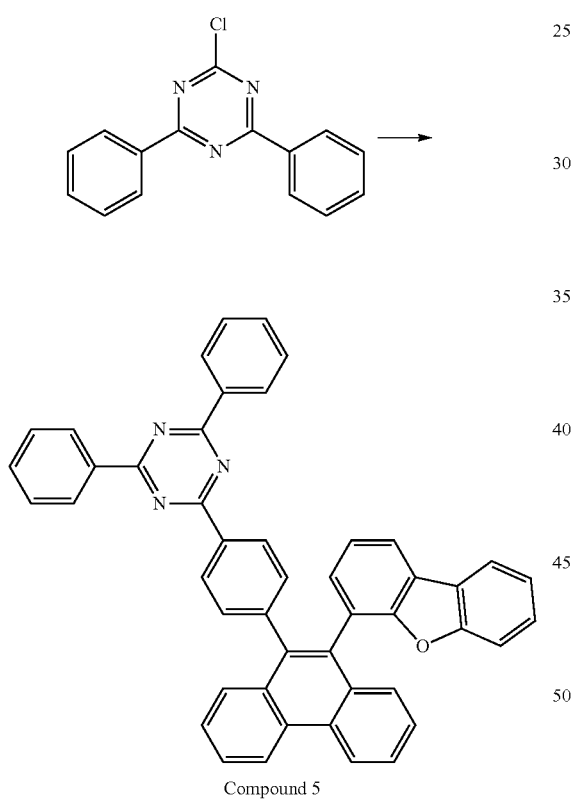

Compound 5

Compound 5 (11 g, yield 50%; MS: [M+H]$^+$=652) was prepared in the same manner as in the preparation of Compound 1, except that Compound E2 (18.4 g, 34 mmol) was used instead of Compound A4.

EXPERIMENTAL EXAMPLE

Experimental Example 1-1

A glass substrate on which a thin film of ITO (indium tin oxide) was coated in a thickness of 1,300 Å was put into distilled water containing the detergent dissolved therein and washed by the ultrasonic wave. In this case, the used detergent was a product commercially available from Fisher Co. and the distilled water was one which had been twice filtered by using a filter commercially available from Millipore Co. The ITO was washed for 30 minutes, and ultrasonic washing was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator.

On the ITO transparent electrode thus prepared, a compound of Formula HI-1 below was thermally vacuum-deposited in a thickness of 50 Å to form a hole injection layer. A compound of Formula HT-1 was thermally vacuum-deposited on the hole injection layer in a thickness of 250 Å to form a hole transport layer, and a compound of Formula HT-2 below was vacuum-deposited on the HT-1 deposition layer in a thickness of 50 Å to form an electron blocking layer. The compound of Formula E1 prepared in Preparation Example 1 and a compound of Formula YGD-1 below as a phosphorescent dopant were vacuum-deposited at a weight ratio of 88:12 on the HT-2 deposition layer to form a light emitting layer having a thickness of 400 Å. Then, a compound of Formula ET-1 below was vacuum-deposited on the light emitting layer in a thickness of 250 Å, and further a compound of Formula ET-2 below was vacuum-deposited with 2 wt % of Li in a thickness of 100 Å to form an electron transport layer and an electron injection layer. Aluminum was deposited on the electron injection layer in a thickness of 1000 Å to form a cathode.

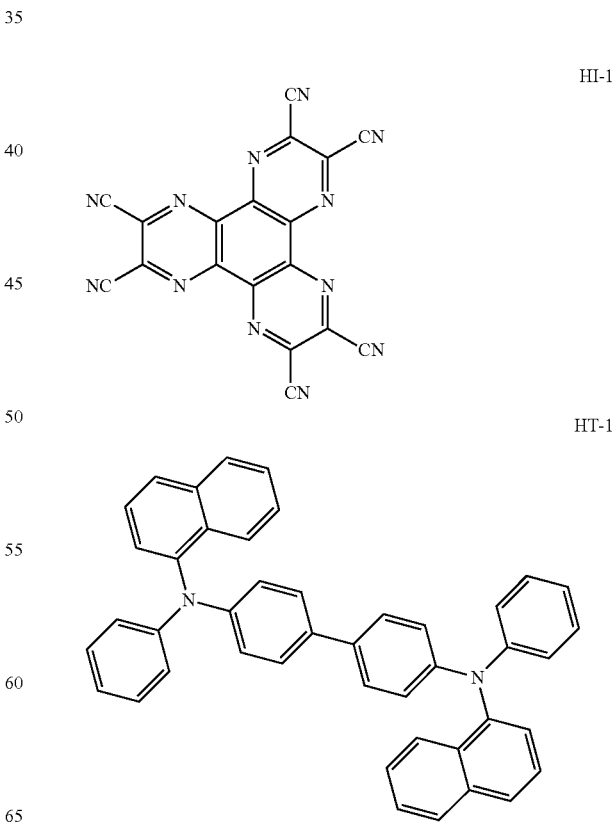

HI-1

HT-1

HT-2

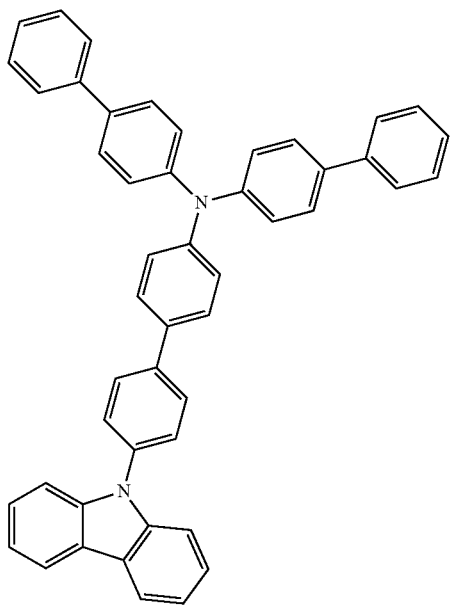

YGD-1

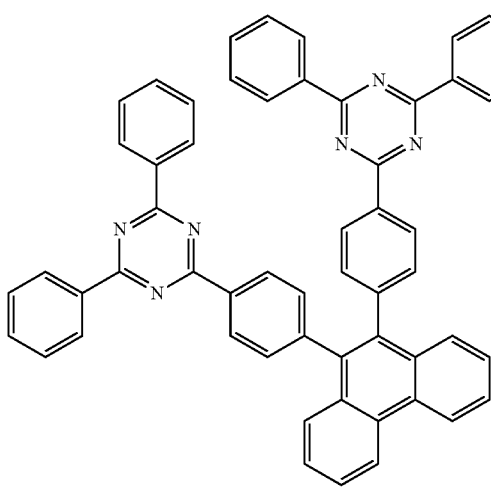

ET-1

ET-2

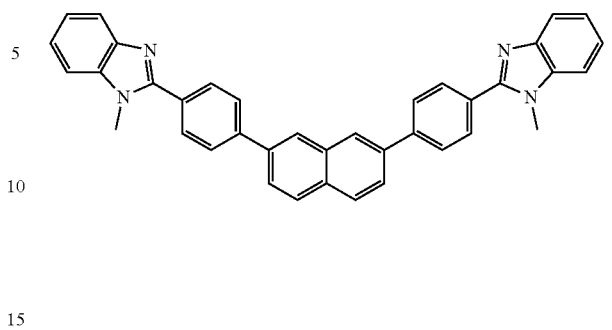

In the above process, the vapor deposition rate of the organic material was maintained at 0.4 to 0.7 Å/sec, the vapor deposition rate of aluminum was maintained at 2 Å/sec, and the degree of vacuum during vapor deposition was maintained at $1\times10^{-7}$~$5\times10^{-8}$ torr.

Experimental Examples 1-2 to 1-5

The organic light emitting device was manufactured in the same manner as in Experimental Example 1-1, except that the compounds shown in Table 1 below was used instead of the compound 1 of Preparation Example 1 in Experimental Example 1-1.

Comparative Experimental Examples 1-1 to 1-3

The organic light emitting devices were manufactured in the same manner as in Experimental Example 1-1, except that the compounds shown in Table 1 below were used instead of the compound 1 of Preparation Example 1 in Experimental Example 1. The compounds of Formulae CE1 to CE3 in Table 1 below are as follows.

CE1

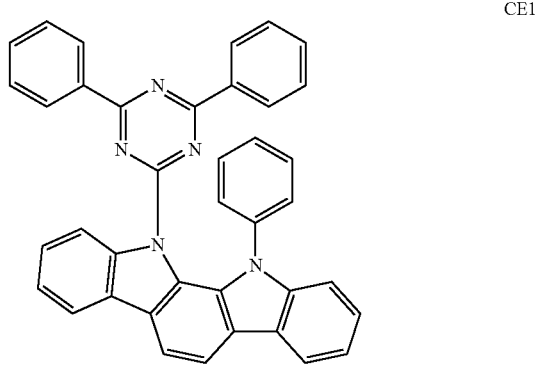

-continued

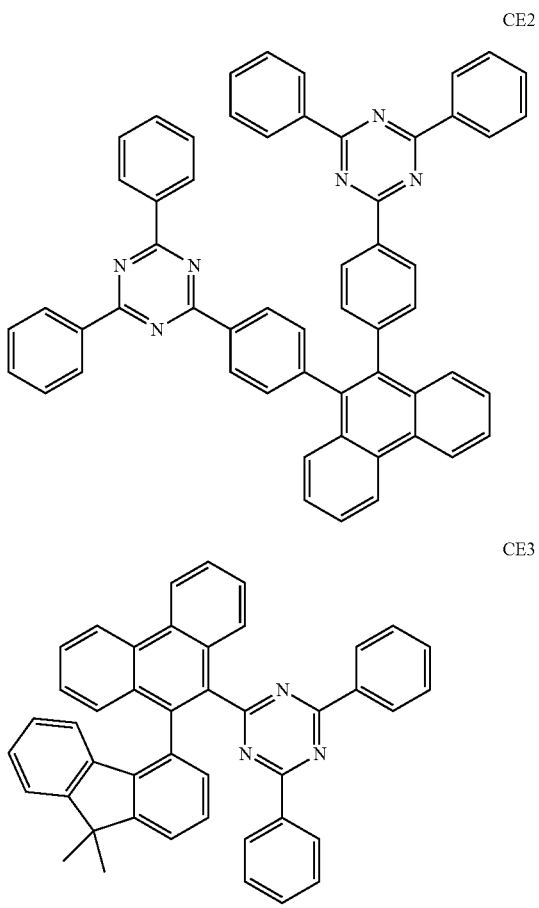

CE2

CE3

The driving voltage and light emitting efficiency were measured at the current density of 10 mA/cm² for the organic light emitting devices manufactured in the Examples and Comparative Examples, and the time (LT95) at which the luminance became 95% relative to the initial luminance at the current density of 50 mA/cm² was measured. The results are shown in Table 1 below.

TABLE 1

| Class | Compound | Voltage (V) (@10 mA/cm²) | Efficiency (Cd/A) (@10 mA/cm²) | Color coor-dinate (x, y) | Lifetime (h) LT95 at 50 mA/cm² |
|---|---|---|---|---|---|
| Experimental Example 1-1 | Compound 1 | 3.5 | 61 | 0.46, 0.53 | 100 |
| Experimental Example 1-2 | Compound 2 | 3.4 | 65 | 0.46, 0.52 | 70 |
| Experimental Example 1-3 | Compound 3 | 3.4 | 62 | 0.46, 0.53 | 95 |
| Experimental Example 1-4 | Compound 4 | 3.4 | 64 | 0.47, 0.52 | 105 |
| Experimental Example 1-5 | Compound 5 | 3.5 | 65 | 0.46, 0.52 | 89 |
| Comparative Experimental Example 1-1 | CE 1 | 3.5 | 70 | 0.46, 0.53 | 60 |
| Comparative Experimental Example 1-2 | CE 2 | 3.5 | 60 | 0.44, 0.55 | 20 |

TABLE 1-continued

| Class | Compound | Voltage (V) (@10 mA/cm²) | Efficiency (Cd/A) (@10 mA/cm²) | Color coor-dinate (x, y) | Lifetime (h) LT95 at 50 mA/cm² |
|---|---|---|---|---|---|
| Comparative Experimental Example 1-3 | CE 3 | 3.5 | 62 | 0.44, 0.55 | 5 |

As shown in Table 1, it was confirmed that, when the compound of the present invention was used as the light emitting layer material, it exhibited excellent efficiency and lifetime as compared with Comparative Experimental Examples.

Experimental Example 2-1

A glass substrate (Corning 7059 Glass) on which a thin film of ITO (indium tin oxide) was coated in a thickness of 1,000 Å was put into distilled water containing the dispersant dissolved therein and washed by the ultrasonic wave. The used detergent was a product commercially available from Fisher Co. and the distilled water was one which had been twice filtered by using a filter commercially available from Millipore Co. The ITO was washed for 30 minutes, and ultrasonic washing was then repeated twice for 10 minutes by using distilled water. After the washing with distilled water was completed, the substrate was ultrasonically washed in the order of isopropyl alcohol, acetone, and methanol solvent, and dried, On the ITO transparent electrode thus prepared, a compound of Formula HI-1 below was thermally vacuum-deposited in a thickness of 500 Å to form a hole injection layer. A compound of Formula HT-1 was vacuum-deposited on the hole injection layer in a thickness of 400 Å to form a hole transport layer, and a host of Formula H1 below and a dopant compound of Formula D1 below were vacuum-deposited in a thickness of 300 Å at a weight ratio of 97.5:2.5 to form a light emitting layer. A compound of Formula ET-A below was vacuum-deposited on the light emitting layer in a thickness of 50 Å to form an electron transport layer. Compound 1 prepared in Preparation Example 1 and LiQ (Lithium Quinolate) were vacuum-deposited at a weight ratio of 1:1 on the electron transport layer to form an electron injection and transport layer having a thickness of 350 Å. Lithium fluoride (LiF) in a thickness of 12 Å and aluminum in a thickness of 2,000 Å were sequentially deposited on the electron injection and transport layer to form a cathode.

HI-1

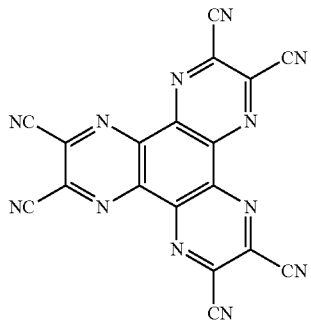

HT-1

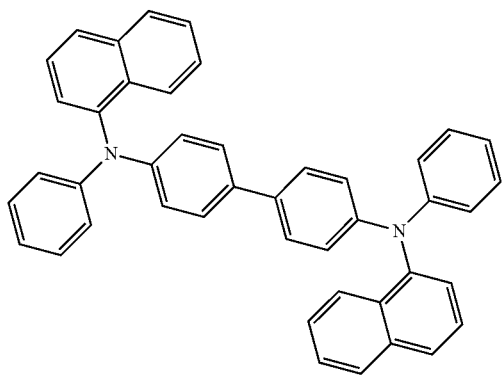

H1

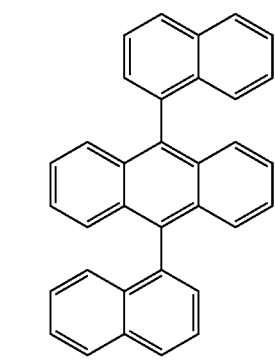

D1

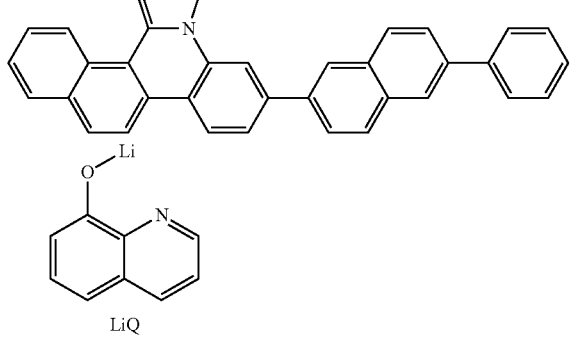

ET-A

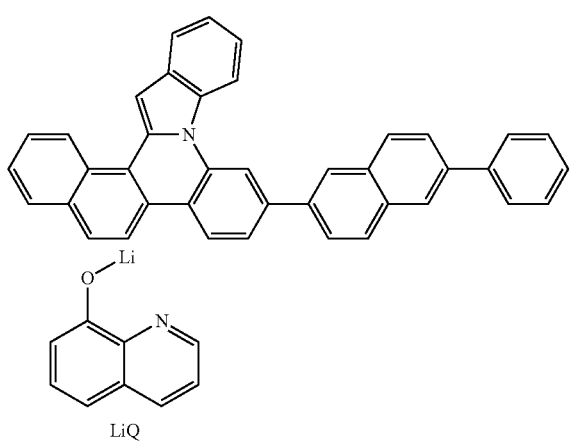

LiQ

In the above process, the vapor deposition rate of the organic material was maintained at 0.4 to 0.7 Å/sec, the vapor deposition rate of lithium fluoride of the cathode was maintained at 0.3 Å/sec, the vapor deposition rate of aluminum was maintained at 2 Å/sec, and the degree of vacuum during vapor deposition was maintained at $2\times10^{-7}$~$5\times10^{-6}$ torr, to thereby manufacture an organic light emitting device.

Experimental Examples 2-2 to 2-5

The organic light emitting devices were manufactured in the same manner as in Experimental Example 2-1, except that the compounds shown in Table 1 below were used instead of the compound 1 of Preparation Example 1 in Experimental Example 2-1.

Comparative Experimental Examples 2-1 to 2-3

The organic light emitting devices were manufactured in the same manner as in Experimental Example 2-1, except that the compounds shown in Table 2 below were used instead of the compound 1 of Preparation Example 1 in Experimental Example 2-1. The compounds of Formulae CE4, CE2 and CE3 in Table 2 below are as follows.

CE4

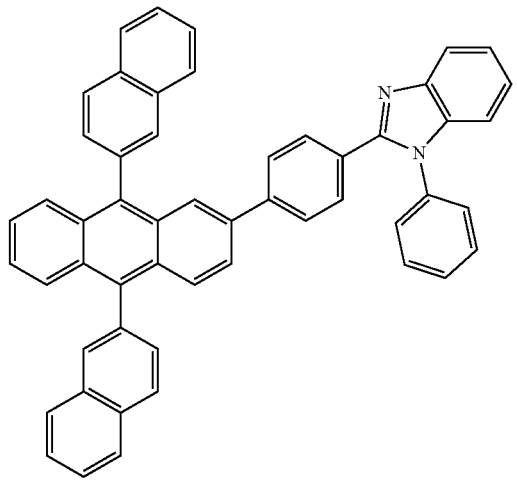

CE2

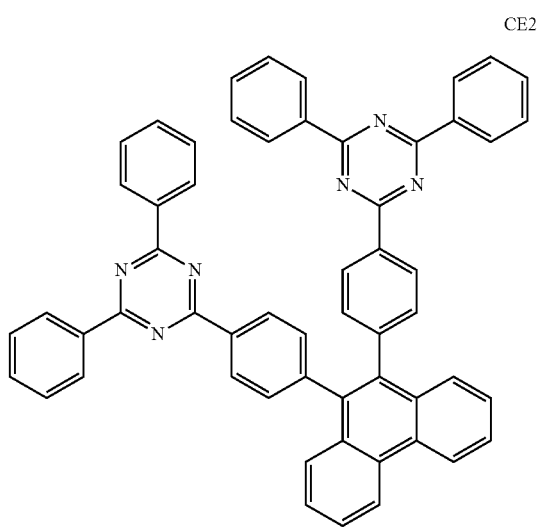

-continued

CE3

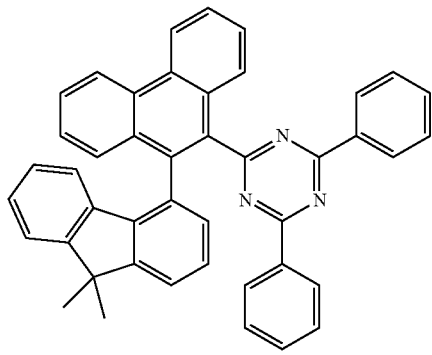

The driving voltage and light emitting efficiency were measured at the current density of 10 mA/cm² for the organic light emitting devices manufactured in the Experimental Examples and Comparative Experimental Examples, and the time (LT95) at which the luminance became 95% relative to the initial luminance at the current density of 50 mA/cm² was measured. The results are shown in Table 2 below.

TABLE 2

| Class | Compound | Voltage (V) (@10 mA/cm²) | Efficiency (Cd/A) (@10 mA/cm²) | Color coordinate (x, y) | Lifetime (h) LT95 at 50 mA/cm² |
|---|---|---|---|---|---|
| Experimental Example 2-1 | Compound 1 | 4.2 | 6.9 | 0.133, 0.133 | 150 |
| Experimental Example 2-2 | Compound 2 | 3.9 | 7.2 | 0.134, 0.132 | 100 |
| Experimental Example 2-3 | Compound 3 | 4 | 7 | 0.134, 0.132 | 145 |
| Experimental Example 2-4 | Compound 4 | 4 | 7.1 | 0.134, 0.132 | 131 |
| Experimental Example 2-5 | Compound 5 | 3.9 | 7.1 | 0.132, 0.134 | 121 |
| Comparative Experimental Example 2-1 | CE 4 | 3.9 | 6.8 | 0.134, 0.133 | 78 |
| Comparative Experimental Example 2-2 | CE 2 | 3.9 | 6.8 | 0.133, 0.133 | 81 |
| Comparative Experimental Example 2-3 | CE 3 | 4.3 | 6.7 | 0.134, 0.132 | 27 |

As shown in Table 2, it was confirmed that, when the compound of the present invention was used as the electron transport layer material, it exhibited excellent efficiency and lifetime as compared with Comparative Experimental Examples.

DESCRIPTION OF SYMBOLS

1: substrate,
3: light emitting layer
5: hole injection layer
6: hole transport layer
7: light emitting layer
8: electron transport layer
2: anode,
4: cathode

The invention claimed is:

1. A compound represented by Formula 1 below:

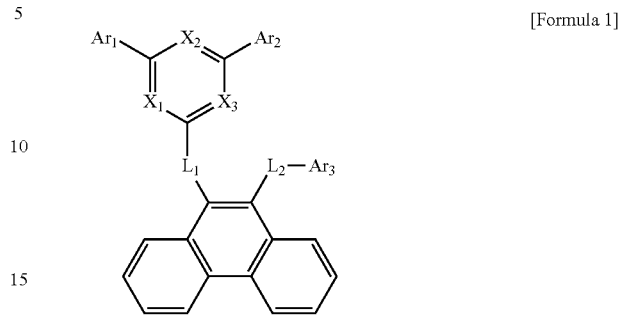

[Formula 1]

in Formula 1 above, $X_1$, $X_2$ and $X_3$ are each independently CH or N, provided that at least one of $X_1$, $X_2$ and $X_3$ is N, $L_1$ is a substituted or unsubstituted $C_{6-60}$ arylene, or a substituted or unsubstituted $C_{5-60}$ heteroarylene containing at least one heteroatom selected from the group consisting of N, O and S, $L_2$ is a single bond, a substituted or unsubstituted $C_{6-60}$ arylene, or a substituted or unsubstituted $C_{5-60}$ heteroarylene containing at least one heteroatom selected from the group consisting of N, O and S, $Ar_1$, $Ar_2$ and $Ar_3$ are each independently a substituted or unsubstituted $C_{6-60}$ aryl, or a substituted or unsubstituted $C_{5-60}$ heteroaryl containing at least one heteroatom selected from the group consisting of N, O and S, wherein said aryl or heteroaryl can be further substituted with a cyano group, and

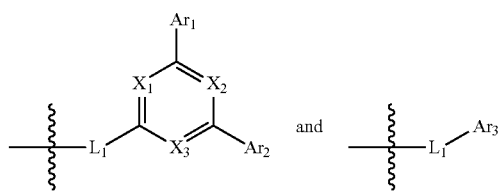

are different from each other.

2. The compound of claim 1, wherein
the compound represented by the Formula 1 is any one selected from compounds represented by Formulas 1-1 to 1-4:

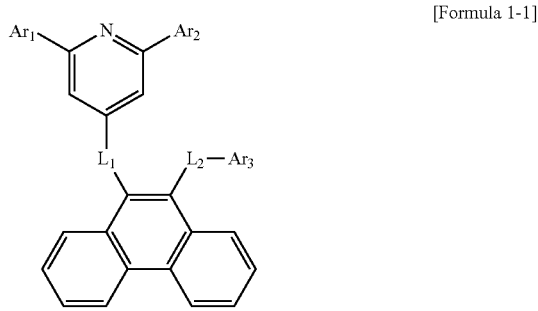

[Formula 1-1]

[Formula 1-2]

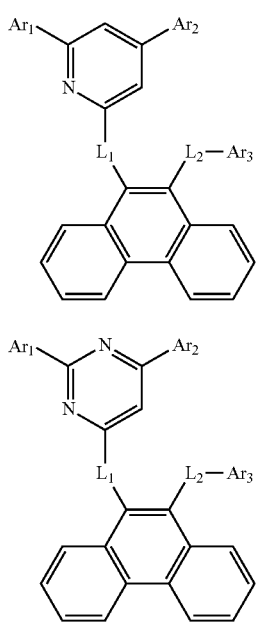

[Formula 1-3]

[Formula 1-4]

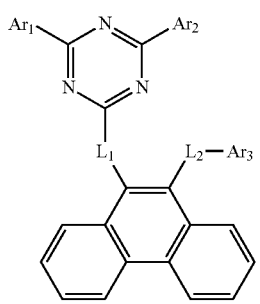

in Formulas 1-1 to 1-4,

L₁, L₂, Ar₁, Ar₂ and Ar₃ are the same as defined in claim 1.

3. The compound of claim 1, wherein L₁ is any one selected from the group consisting of the following:

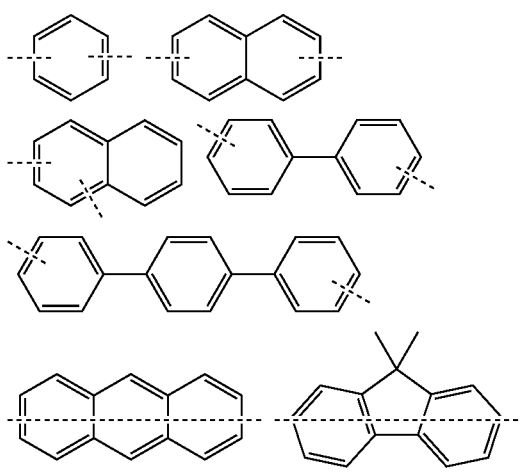

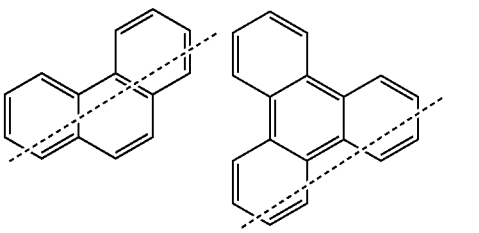

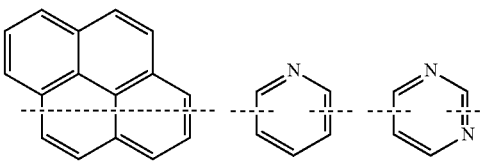

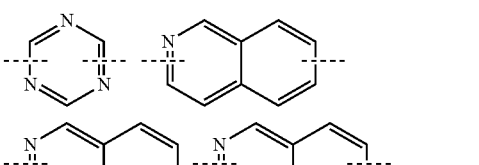

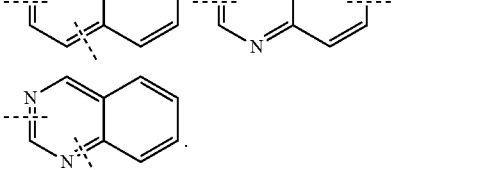

4. The compound of claim 1, wherein L₁ is any one selected from the group consisting of the following:

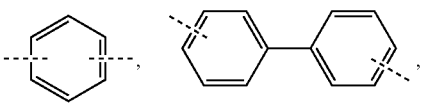

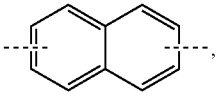

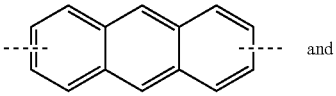 and

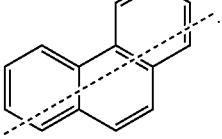

5. The compound of claim 1, wherein L₂ is a single bond or any one selected from the group consisting of the following:

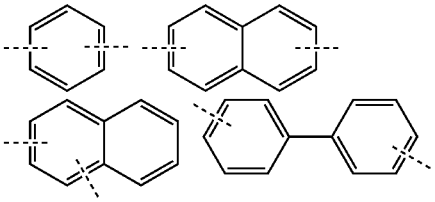

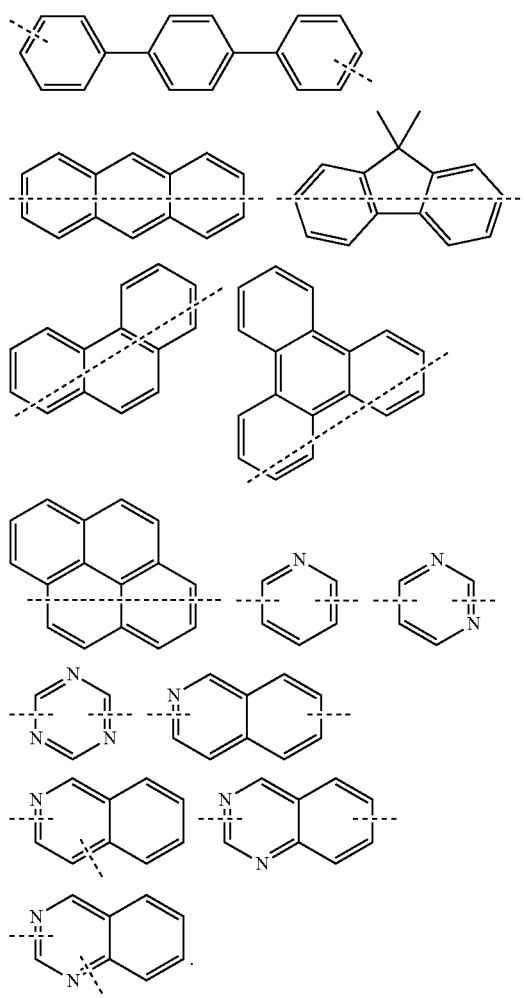
6. The compound of claim 1, wherein $L_2$ is any one selected from the group consisting of a single bond,
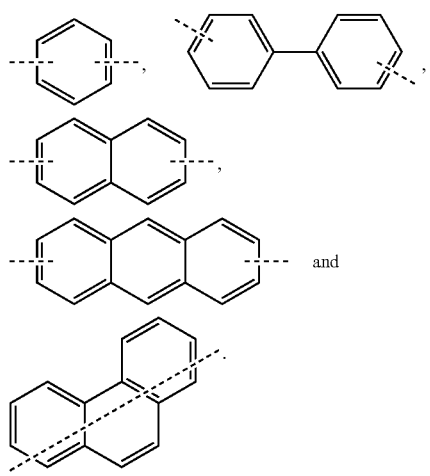
and
7. The compound of claim 1, wherein $Ar_1$, $Ar_2$ and $Ar_3$ are each independently any one selected from the group consisting of the following:
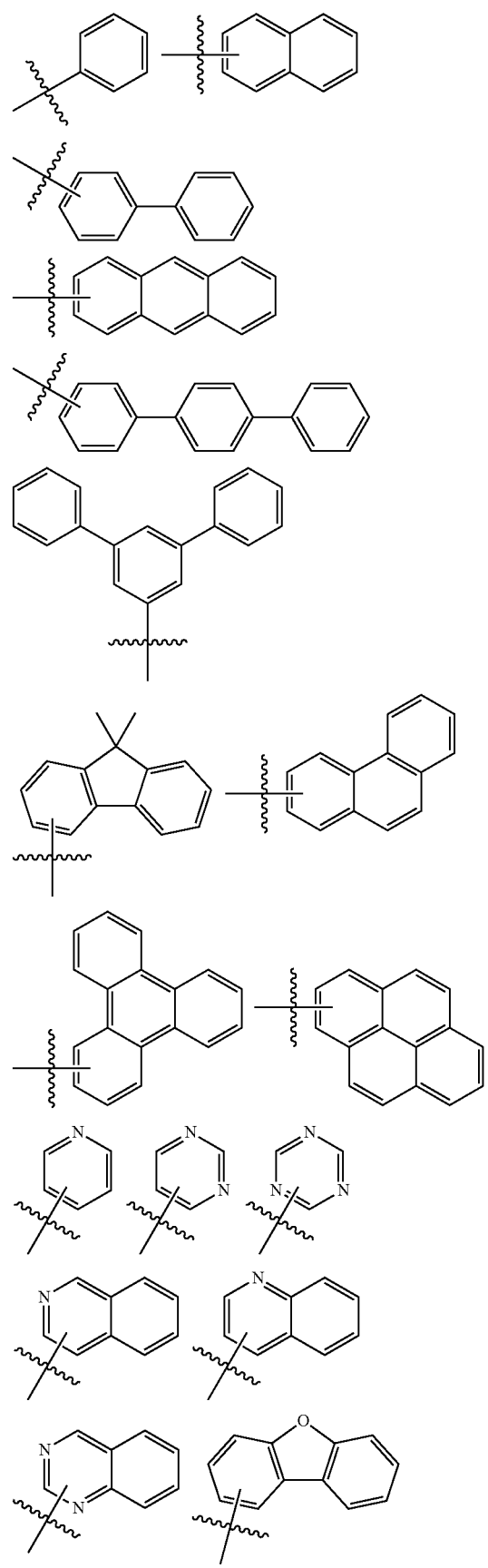

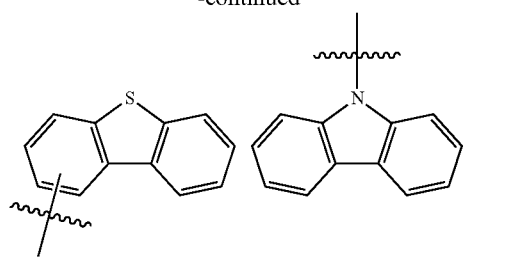
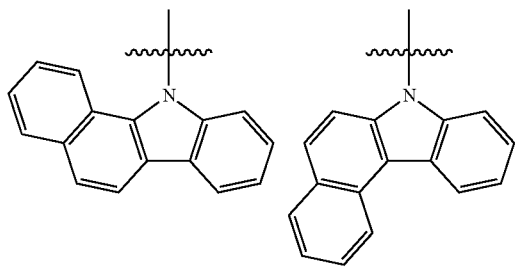
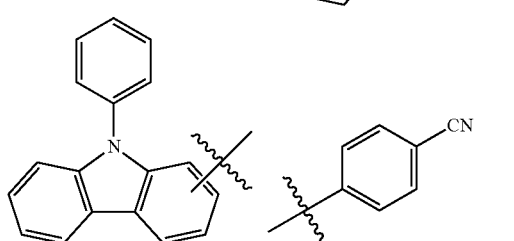
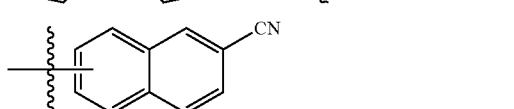
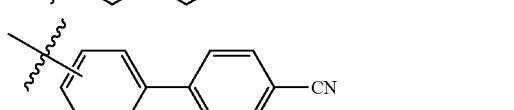
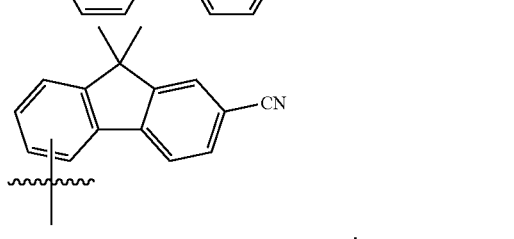
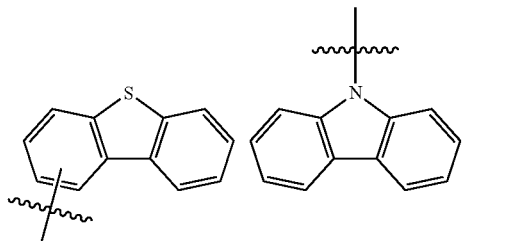
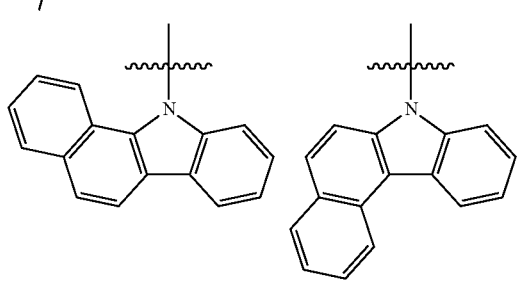
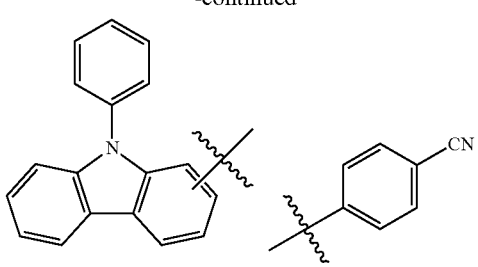
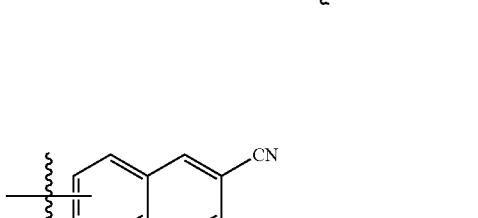
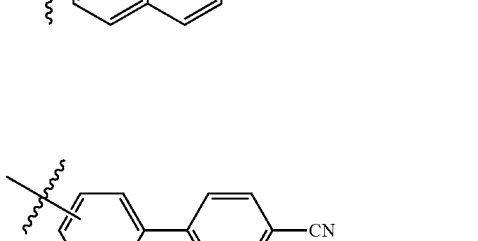
8. The compound of claim 1, wherein the compound represented by the Formula 1 is any one selected from the group consisting of the following:
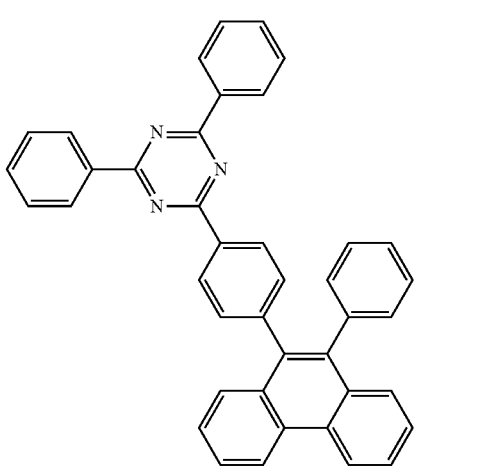

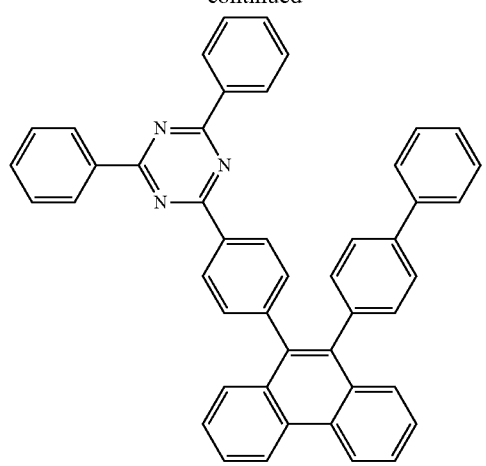
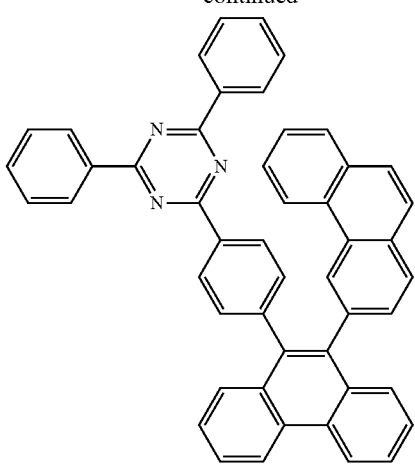
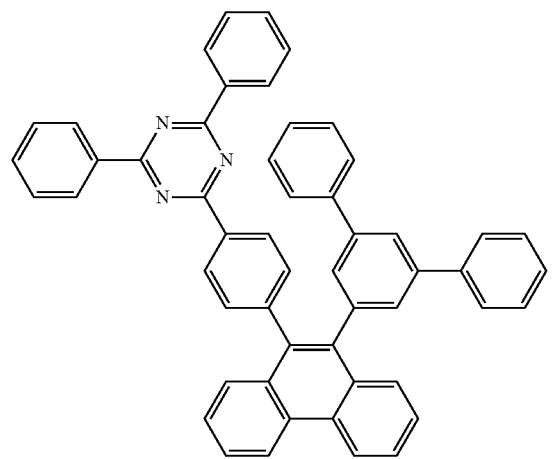
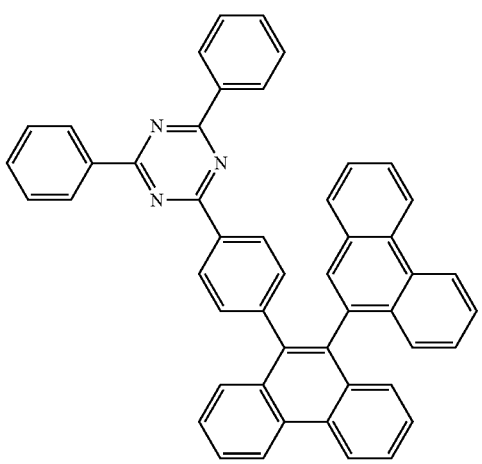
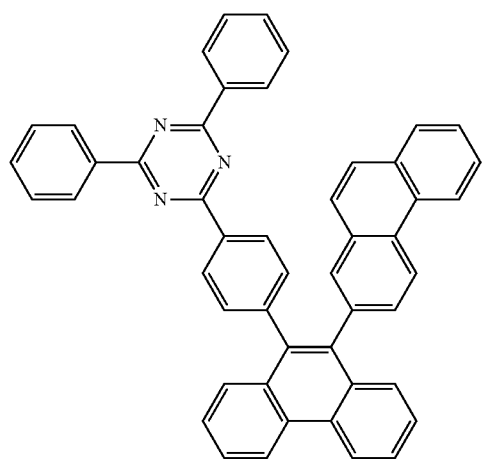
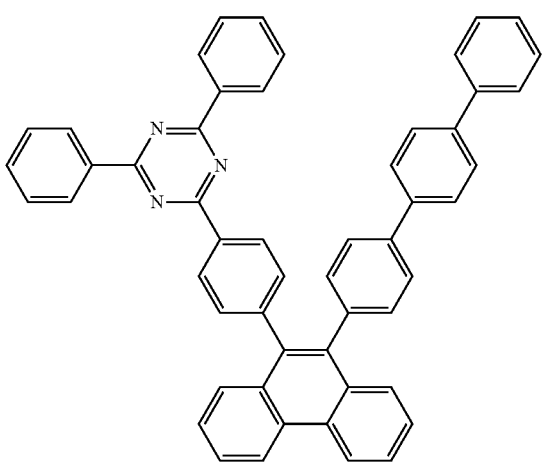

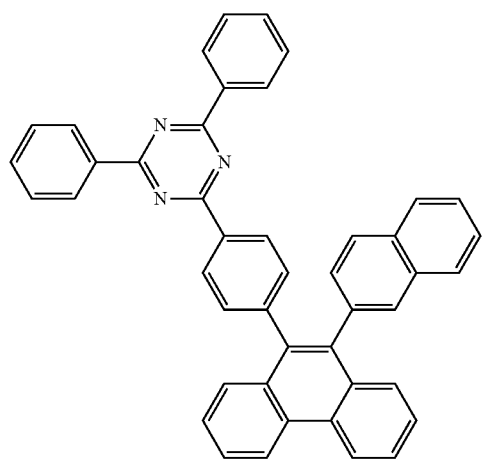
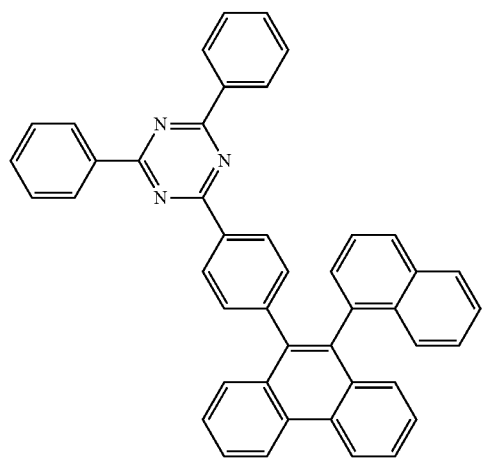
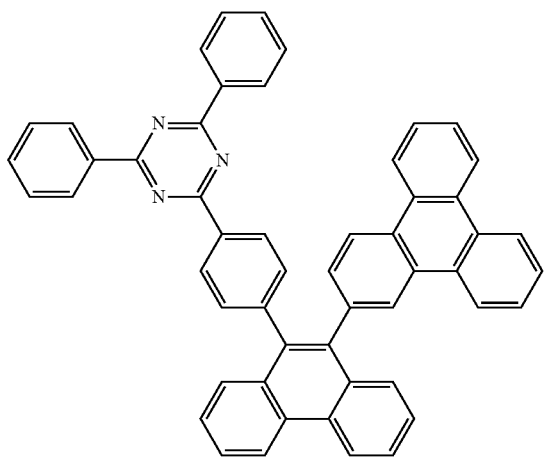
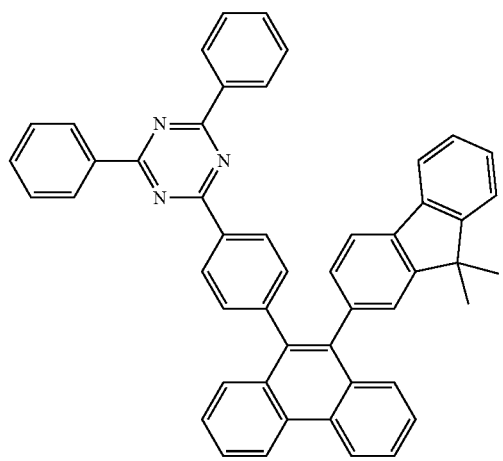
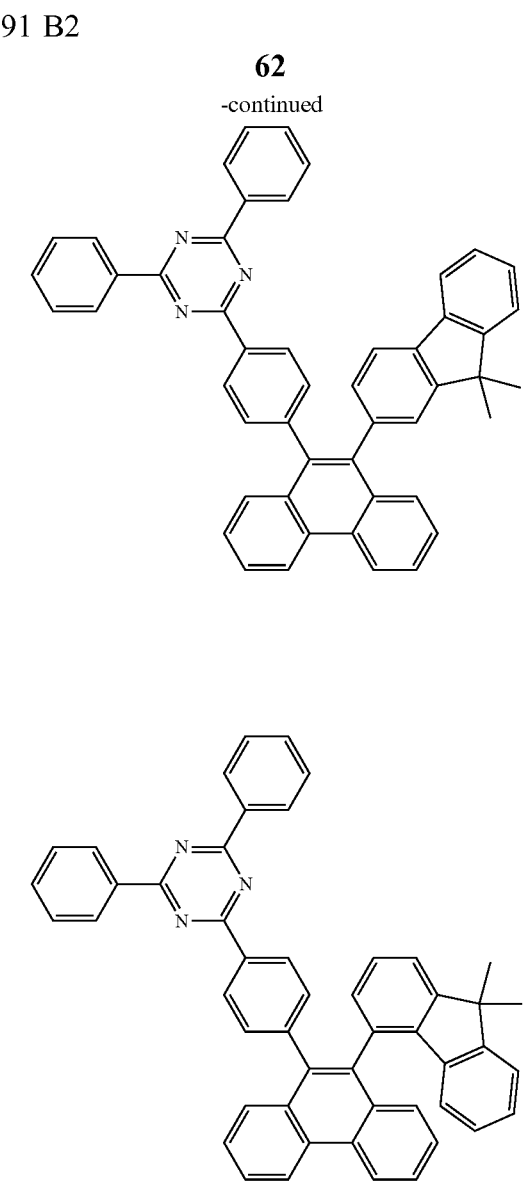

63
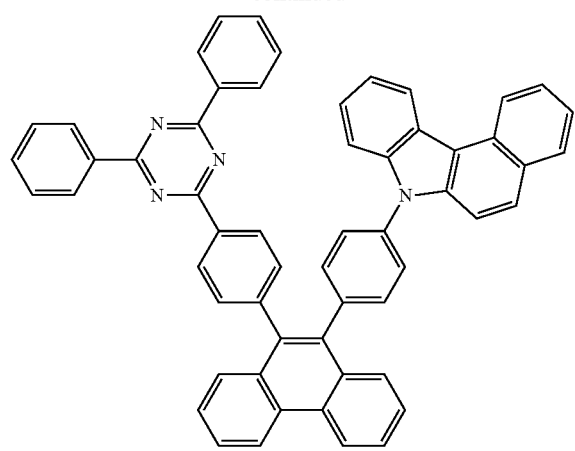
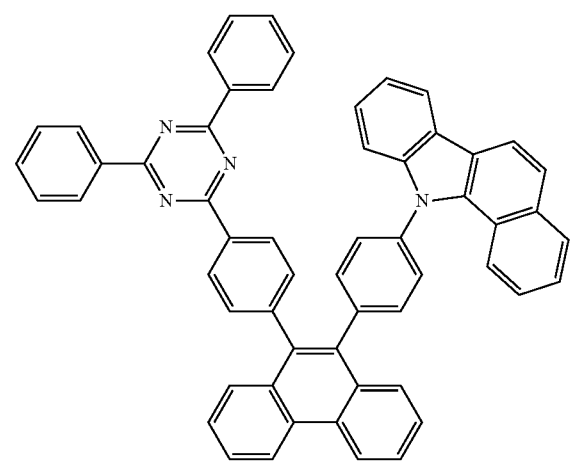
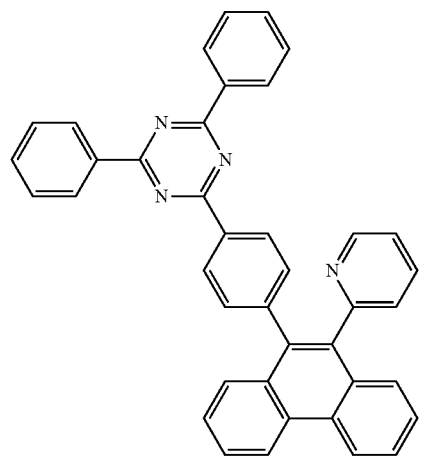
64
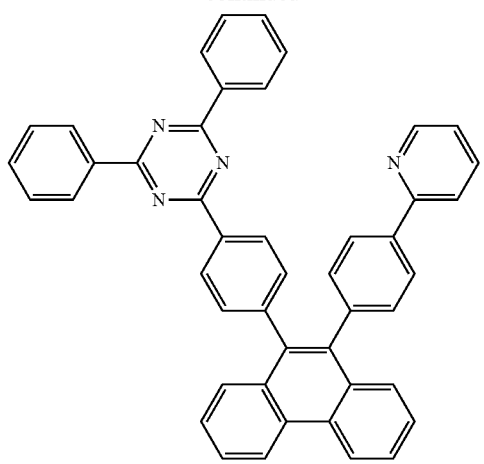
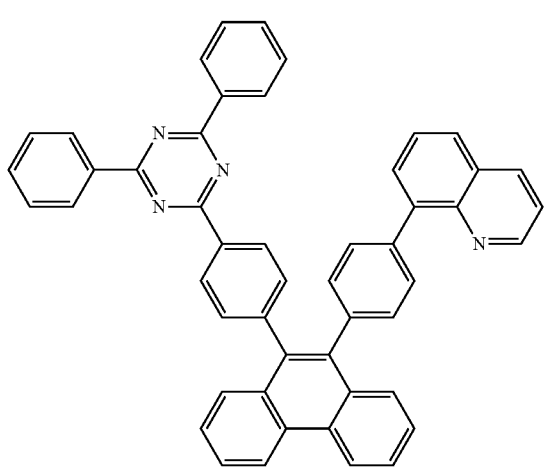
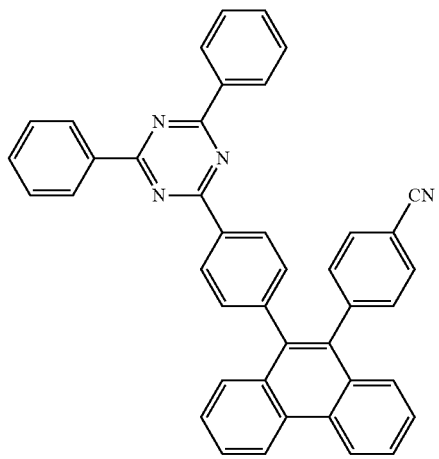

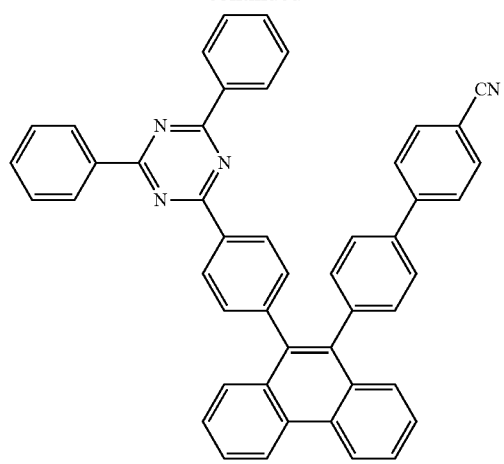
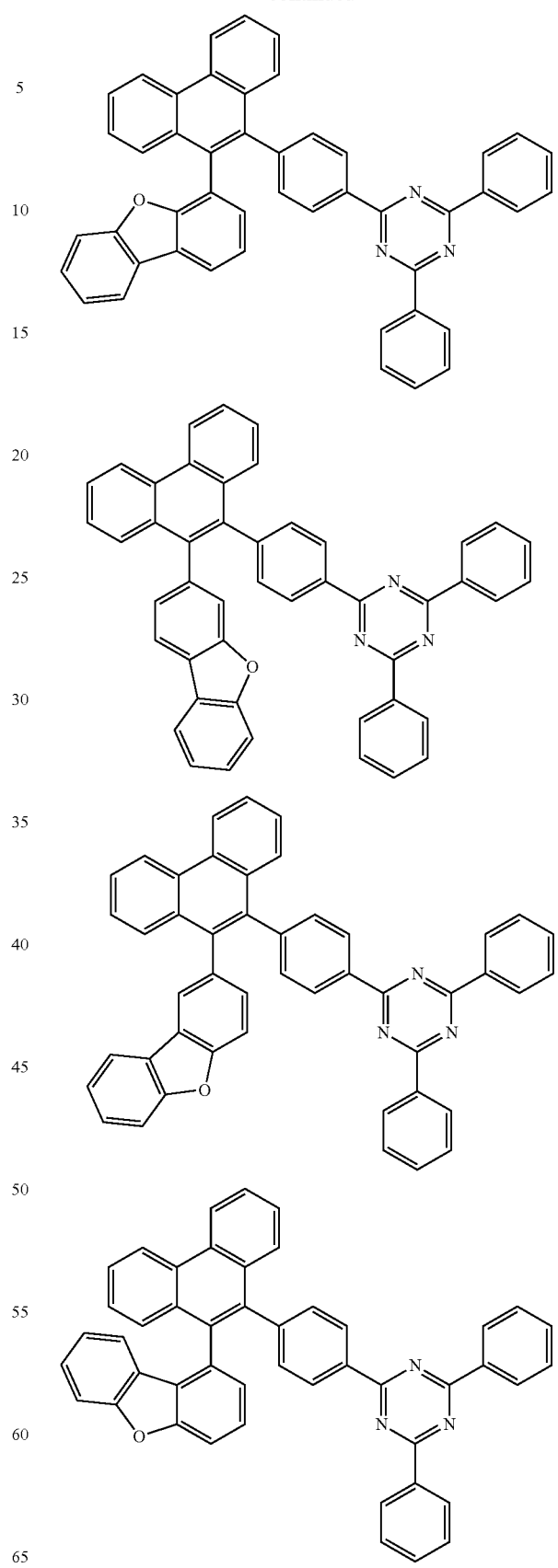

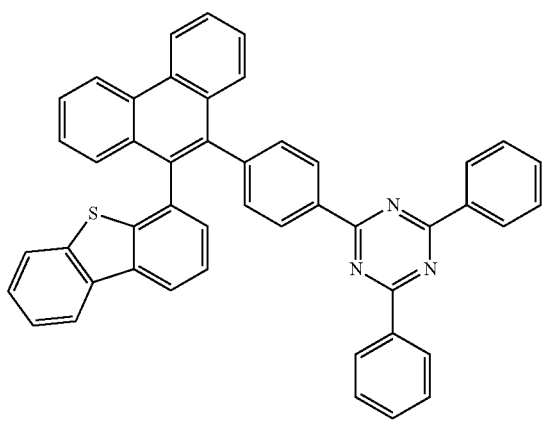
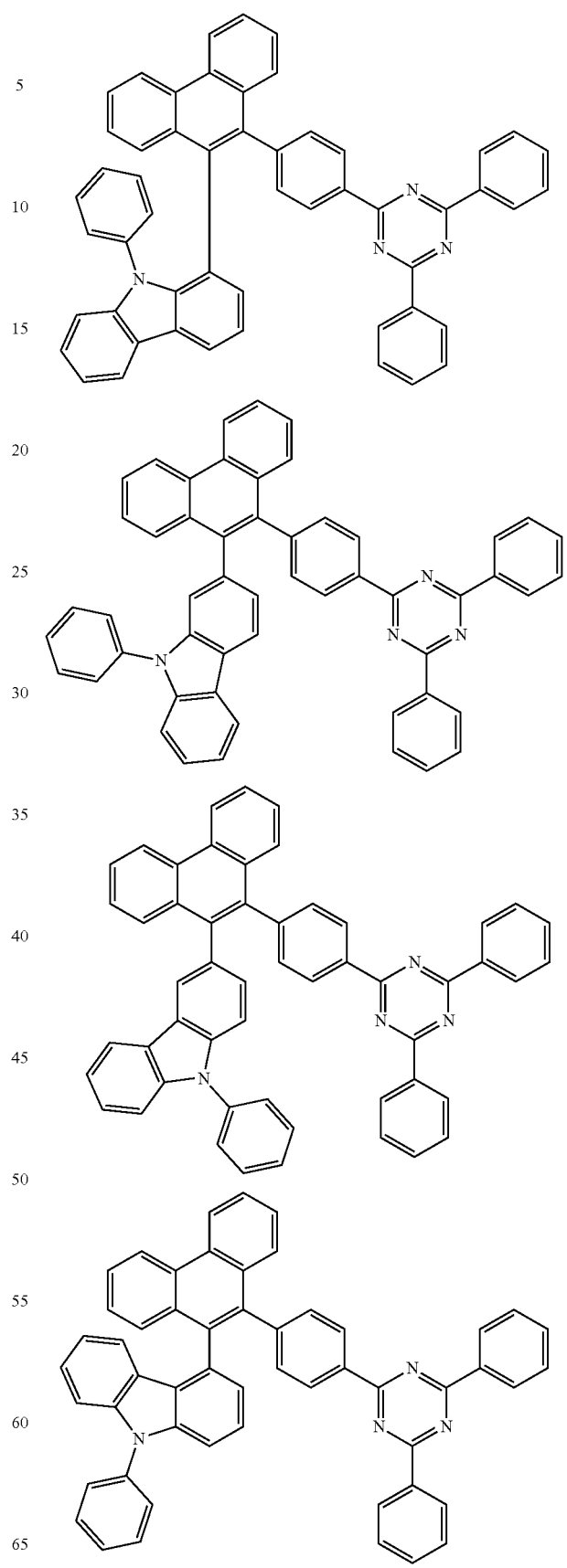

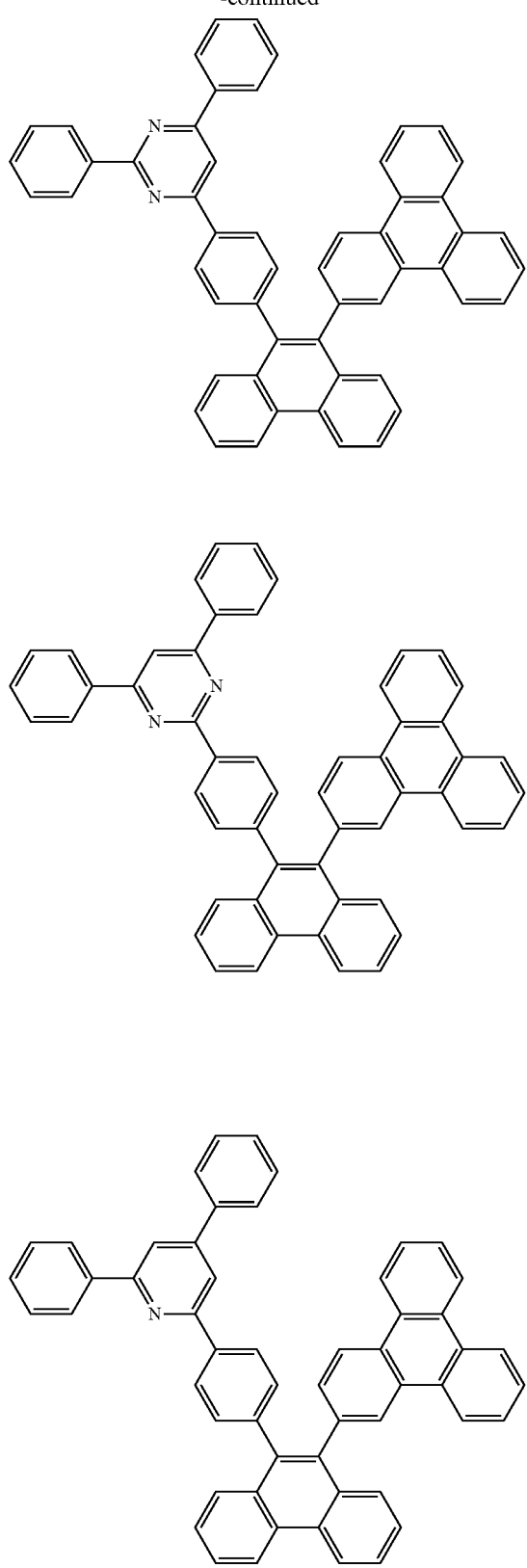
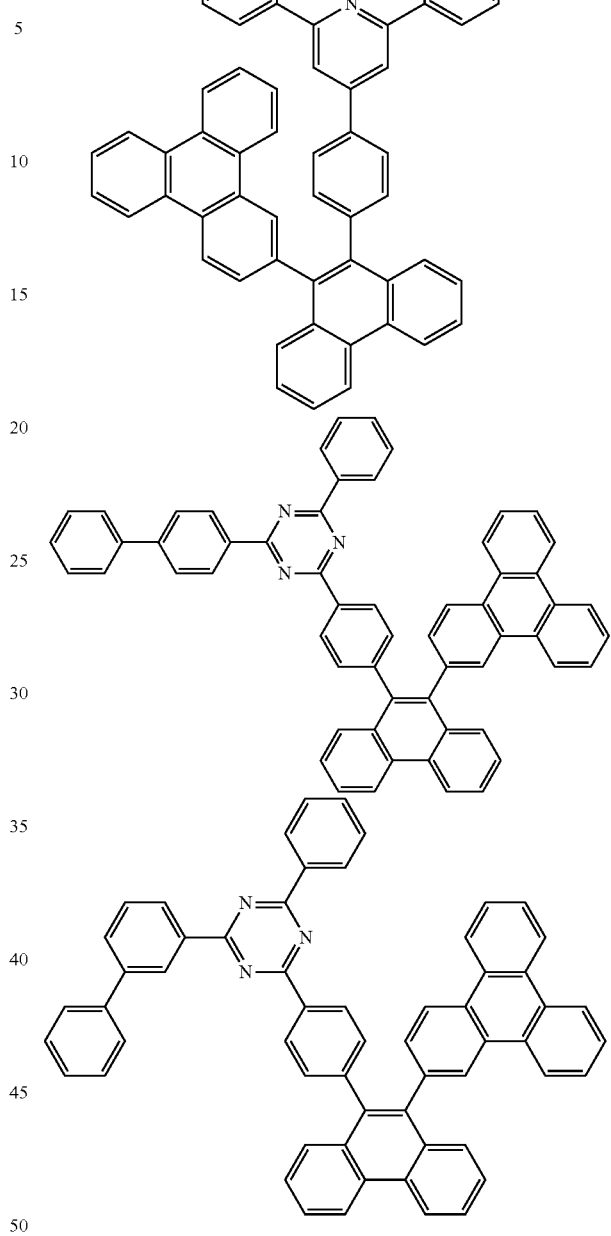

9. An organic light entitling device comprising a first electrode; a second electrode provided to face the first electrode; and one or more organic material layers provided between the first electrode and the second electrode, wherein at least one of the one or more organic material layers includes a compound according to claim 1.

10. The organic light emitting device of claim 9, wherein the at least one of the one or more organic material layers comprising the compound is an electron injection layer; an electron transport layer; or a layer simultaneously performing electron injection and electron transport.

* * * * *